United States Patent [19]
Biesecker et al.

[11] Patent Number: 6,140,490
[45] Date of Patent: Oct. 31, 2000

[54] HIGH AFFINITY NUCLEIC ACID LIGANDS OF COMPLEMENT SYSTEM PROTEINS

[75] Inventors: Gregory Biesecker; Larry Gold, both of Boulder, Colo.

[73] Assignee: NeXstar Pharmaceuticals, Inc., Boulder, Colo.

[21] Appl. No.: 09/023,228

[22] Filed: Feb. 12, 1998

Related U.S. Application Data

[63] Continuation-in-part of application No. PCT/US97/01739, Jan. 30, 1997, which is a continuation-in-part of application No. 08/595,335, Feb. 1, 1996, abandoned.

[51] Int. Cl.[7] .............................. C07H 21/04; C12Q 1/68; C12P 19/34
[52] U.S. Cl. ..................... 536/24.31; 435/6; 435/91.2; 536/23.1; 536/25.4
[58] Field of Search .................... 435/6, 91.2; 536/23.1, 536/24.3, 25.41; 935/77, 78

[56] References Cited

U.S. PATENT DOCUMENTS

| | | | |
|---|---|---|---|
| 5,270,163 | 12/1993 | Gold et al. | 435/6 |
| 5,428,149 | 6/1995 | Eaton et al. | 435/6 |
| 5,459,015 | 10/1995 | Janjic et al. | 435/6 |
| 5,472,841 | 12/1995 | Jayasena et al. | 435/6 |
| 5,476,766 | 12/1995 | Gold et al. | 435/6 |
| 5,496,938 | 3/1996 | Gold et al. | 435/6 |
| 5,503,978 | 4/1996 | Schneider et al. | 435/6 |
| 5,527,894 | 6/1996 | Gold et al. | 435/6 |
| 5,543,293 | 8/1996 | Gold et al. | 435/6 |
| 5,567,588 | 10/1996 | Gold et al. | 435/6 |

FOREIGN PATENT DOCUMENTS

| | | |
|---|---|---|
| 2 183 661 | 6/1987 | United Kingdom . |
| WO 89/06694 | 7/1989 | WIPO . |
| WO 92/14843 | 9/1992 | WIPO . |
| WO 97/42317 | 11/1997 | WIPO . |

OTHER PUBLICATIONS

Szostak, "Structure and Activity of Ribozymes," in *Redesigning the Molecules of Life*, (S.A. Benner ed.) Springer–Verlag Berlin Heidelberg, pp. 87–113, (1988).
Joyce, Gene, 82:83 (1989).
Joyce et al., Nucleic Acids Research 17:711 (1989).
Ellington and Szostak, Abstract of papers presented at the 1990 meeting on RNA Processing, Cold Spring Harbor Laboratory, Cold Spring Harbor, N.Y., p. 84 (1990).
Kinzler et al., Nucleic Acids Research 17:3645 (1989).
Kramer et al., J. Mol. Biol., 89:719 (1974).
Levisohn et al., Proc. Natl. Acad. Sci. USA, 63(3):805 (1969).
Levisohn et al., Proc. Natl. Acad. Sci. USA 60:866 (1968).
Oliphant et al., Mol. Cell. Biol. 9:2944 (1989).
Oliphant et al., Nucleic Acids Research, 16:7673 (1988).
Oliphant et al., Methods in Enzymology 155:568 (1987).
Oliphant et al., Gene, 44:177 (1986).
Robertson et al., Nature, 344:467 (1990).
Thiesen et al., Nucleic Acids Research, 18:3203 (1990).
Eikelenboom et al., Acta Neuropath., 57:239–242 (1982).
Schravendijk et al., Mol. Immunol., 19:1179–1187 (1982).
Rosenberg et al., J. Rheumatol., 15:1091–1096 (1988).
Biesecker, Molecular Immunology, 33 (Supl. 1) 86 (1996).

*Primary Examiner*—Stephanie Zitomer
*Attorney, Agent, or Firm*—Swanson & Bratschun LLC

[57] ABSTRACT

Methods are described for the identification and preparation of high-affinity Nucleic Acid Ligands to Complement System Proteins. Methods are described for the identification and preparation of high affinity Nucleic Acid Ligands to Complement System Proteins C1q, C3 and C5. Included in the invention are specific RNA ligands to C1q, C3 and C5 identified by the SELEX method.

3 Claims, 3 Drawing Sheets

SEQ ID NO: 75

HIGH AFFINITY NUCLEIC ACID LIGANDS OF COMPLEMENT SYSTEM PROTEINS

RELATED APPLICATIONS

This application is a Continuation-in-Part of PCT/US97/01739, filed Jan. 30, 1997, entitled "High Affinity Nucleic Acid Ligands of Complement System Proteins," which is a Continuation-in-Part of U.S. patent application Ser. No. 08/595,335, filed Feb. 1, 1996, entitled "High Affinity Nucleic Acid Ligands of Complement System Proteins," now abandoned.

FIELD OF THE INVENTION

Described herein are methods for identifying and preparing high-affinity Nucleic Acid Ligands to Complement System Proteins. The method utilized herein for identifying such Nucleic Acid Ligands is called SELEX, an acronym for Systematic Evolution of Ligands by EXponential enrichment. Described herein are methods for identifying and preparing high-affinity Nucleic Acid Ligands to the Complement System Proteins C1q, C3 and C5. This invention includes high affinity Nucleic Acid Ligands of C1q, C3 and C5. Also disclosed are RNA ligands of C1q, C3 and C5. Also disclosed are Nucleic Acid Ligands that inhibit and/or activate the Complement System. The oligonucleotides of the present invention are useful as pharmaceuticals or diagnostic agents.

BACKGROUND OF THE INVENTION

The complement system comprises a set of at least 20 plasma and membrane proteins that act together in a regulated cascade system to attack extracellular forms of pathogens (Janeway et al. (1994) *Immunobiology: The Immune System in Health and Disease.* Current Biology Ltd, San Francisco, pp. 8:35–8:55; Morgan (1995) Crit. Rev. in Clin Lab. Sci. 32(3):265–298). There are two distinct enzymatic activation cascades, the classical and alternative pathways, and a non-enzymatic pathway known as the membrane attack pathway.

The classical pathway is usually triggered by an antibody bound to a foreign particle. It comprises several components, C1, C4, C2, C3 and C5 (listed by order in the pathway). Initiation of the classical pathway of the Complement System occurs following binding and activation of the first complement component (C1) by both immune and non-immune activators (Cooper (1985) Adv. Immunol. 37:151). C1 comprises a calcium-dependent complex of components C1q, C1r and C1s, and is activated through binding of the C1q component. C1q contains six identical subunits and each subunit comprises three chains (the A, B and C chains). Each chain has a globular head region which is connected to a collagen-like tail. Binding and activation of C1q by antigen-antibody complexes occurs through the C1 q head group region. Numerous non-antibody C1q activators, including proteins, lipids and nucleic acids (Reid et al. (1993) The Natural Immune System: Humoral Factors. E. Sim, ed. IRL Press, Oxford, p. 151) bind and activate through a distinct site on the collagen-like stalk region.

Non-antibody C1q protein activators include C-reactive protein (CRP) (Jiang et al. (1991) J. Immunol. 146:2324) and serum amyloid protein (SAP) (Bristow et al. (1986) Mol. Immunol. 23:1045); these will activate C1q when aggregated by binding to phospholipid or carbohydrate, respectively. Monomeric CRP or SAP do not activate C1q. C1q is also activated through binding to aggregated β-amyloid peptide (Schultz et al. (1994) Neurosci. Lett. 175:99; Snyder etal. (1994) Exp. Neurol. 128:136), a component of plaques seen in Alzheimer's disease (Jiang et al. (1994) J. Immunol. 152:5050; Eikelenboom et al. (1982) Acta Neuropath. 57:239; Eikelenboom et al. (1989) Virchows Arch. [B] 56:259; Rogers et al. (1992) Proc. Natl. Acad. Sci. USA 89:10016; Dietzschold etal. (1995) J. Neurol. Sci. 130:11). C1q activation might also exacerbate the tissue damage associated with Alzheimer's disease. These activators bind C1q on its collagen-like region, distant from the head-group region where immunoglobulin activators bind. Other proteins which bind the C1 q collagen-like region include collagen (Menzel et al. (1981) Biochim. Biophys. Acta 670:265), fibronectin (Reid et al. (1984) Acta Pathol. Microbiol. Immunol. Scand. Sect. C 92 (Suppl. 284:11), laminin (Bohnsack et al. (1985) Proc. Natl. Acad. Sci. USA 82:3824), fibrinogen and fibrin (Entwistle et al. (1988) Biochem. 27:507), HIV rsgp4l (Stoiber et al. (1995) Mol. Immunol. 32:371), actin (Nishioka et al. (1982) Biochem. Biophys. Res. Commun. 108:1307) and tobacco glycoprotein (Koethe et al. (1995) J. Immunol. 155:826).

C1q also binds and can be activated by anionic carbohydrates (Hughes-Jones et al. (1978) Immunology 34:459) including mucopolysaccharides (Almeda et al. (1983) J. Biol. Chem. 258:785), fucans (Blondin et al. (1994) Mol. Immunol. 31:247) proteoglycans (Silvestri et al. (1981) J. Biol. Chem. 256:7383), and by lipids including lipopolysaccharide (LPS) (Zohair et al. (1989) Biochem. J. 257:865; Stoiber et al. (1994) Eur. J. Immunol. 24:294). Both DNA (Schravendijk et al. (1982) Mol. Immunol. 19:1179; Rosenberg et al. (1988) J. Rheumatol. 15:1091; Uwatoko et al. (1990) J. Immunol. 144:3484) and RNA (Acton et al. (1993) J. Biol. Chem. 268:3530) can also bind and potentially activate C1q. Intracellular components which activate C1q include cellular and subcellular membranes (Linder (1981) J. Immunol. 126:648; Pinckard et al. (1973) J. Immunol. 110: 1376; Storrs et al. (1981) J. Biol. Chem. 256:10924; Giclas et al. (1979) J. Immunol. 122:146; Storrs et al. (1983) J. Immunol. 131:416), intermediate filaments (Linder et al. (1979) Nature 278:176), and actin (Nishioka, supra). All of these interactions would recruit the classical pathway for protection against bacterial (or viral) infection, or as a response to tissue injury (Li et al. (1994) J. Immunol. 152:2995) in the absence of antibody.

A binding site for non-antibody activators including CRP (Jiang et al. (1991) J. Immunol. 146:2324), SAP (Ying et al. (1993) J. Immunol. 150:169), β-amyloid peptide (Newman (1994) Curr. Biol. 4:462) and DNA (Jiang et al. (1992) J. Biol. Chem. 267:25597) has been localized to the amino terminus of C1q A chain at residues 14–26. A synthetic peptide comprising this sequence effectively inhibits both binding and activation. The peptide 14–26 contains several basic residues and matches one of the heparin binding motifs (Yabkowitz et al. (1989) J. Biol. Chem. 264:10888; Cardin et al. (1989) Arteriosclerosis 9:21). The peptide is also highly homologous with peptide 145–156 in collagen-tailed acetylcholinesterase; this site is associated with heparin-sulfate basement membrane binding (Deprez et al. (1995) J. Biol. Chem. 270:11043). A second C1q A chain site at residues 76–92 also might be involved in weaker binding; this site is at the junction of the globular head region and the collagen-like tail.

The second enzymatically activated cascade, known as the alternative pathway, is a rapid, antibody-independent route for the Complement System activation and amplification. The alternative pathway comprises several components, C3, Factor B, and Factor D. Activation of the alternative pathway occurs when C3b, a proteolytic cleavage form of C3, is bound to an activating surface such as a bacterium. Factor B is then bound to C3b, and then Factor B is cleaved by Factor D to yield the active enzyme, Ba. The enzyme Ba then cleaves more C3 to C3b, producing extensive deposition of C3b-Ba complexes on the activating surface. When a second C3b is deposited, forming a C3b-C3b-Ba complex, the enzyme can then cleave C5 and trigger activation of the terminal pathway.

The non-enzymatic terminal pathway, also known as the membrane attack pathway, comprises the components C5, C6, C7, C8 and C9. Activation of this membrane attack pathway results when the C5 component is enzymatically cleaved by either the classical or alternative pathway to yield the small C5a polypeptide and the large C5b fragment. The C5a molecule can trigger a variety of biological responses including leukocyte chemotaxis, smooth muscle contraction, and activation of intracellular signal transduction pathways. The larger C5b fragment binds sequentially to later components to form the C5b-9 membrane attack complex. The C5b-9 membrane attack complex can directly lyse cells. In addition, the C5b-9 membrane attack complex can stimulate cells such as endothelial cells and platelets without causing cell lysis. The non-lytic effects of C5a and C5b-9 are sometimes quite similar.

The Complement System has an important role in defense against bacterial and viral infection, and possibly in immune surveillance against tumors. This is demonstrated most clearly in humans who are deficient in complement components. Individuals deficient in early components (C1, C4, C2 or C3) suffer from recurrent infections, while individuals deficient in late components (C5 through C9) are susceptible to nisseria infection. Complement classical pathway is activated on bacteria by antibodies, by binding of CRP or SAP, or by direct activation through LPS. Complement alternative pathway is activated through binding of C3 to the cell coat. Complement can be activated by viruses through antibodies, and can also be activated on viral infected cells because these are recognized as foreign. In a similar way, transformed cells can be recognized as foreign and can be lysed by the Complement System or targeted for immune clearance.

Activation of the Complement System can and has been used for therapeutic purposes. Antibodies which were produced against tumor cells were then used to activate the Complement System and cause tumor rejection. Also, the Complement System is used together with polyclonal or monoclonal antibodies to eliminate unwanted lymphocytes. For example, anti-lymphocyte globulin or monoclonal anti-T-cell antibodies are used prior to organ transplantation to eliminate lymphocytes which would otherwise mediate rejection.

Although the Complement System has an important role in the maintenance of health, it has the potential to cause or contribute to disease. The Complement System has been implicated in numerous renal, rheumatological, neurological, dermatological, hematological, vascular/pulmonary, allergy, infectious, biocompatibility/shock and other diseases or conditions (Morgan (1995) Crit. Rev. in Clin Lab. Sci. 32(3):265–298; Matis and Rollins (1995) Nature Medicine 1(8):839–842). The Complement System is not necessarily the only cause of the disease state, but it may be one of several factors, each of which contributes to pathogenesis.

Several pharmaceuticals have been developed that inhibit the Complement System in vivo, however, many cause toxicity or are poor inhibitors (Morgan, supra). Heparins, K76COOH and nafamstat mesilate have been shown to be effective in animal studies (Morgan, supra). Recombinant forms of naturally occurring inhibitors of the Complement System have been developed or are under consideration, and these include the membrane regulatory proteins Complement Receptor 1 (CR1), Decay Accelerating Factor (DAF), Membrane Cofactor Protein (MCP) and CD59.

C5 is an attractive target for the development of a Complement System inhibitor, as both the classical and alternative pathways converge at component C5 (Matis and Rollins, supra). In addition, inhibition of C5 cleavage blocks both the C5a and the C5b effects on leukocytes and on tissue such as endothelial cells (Ward (1996) Am. J. Pathol. 149:1079); thus C5 inhibition can have therapeutic benefits in a variety of diseases and situations, including lung inflammation (Mulligan et al. (1998) J. Clin. Invest. 98:503), extracorporeal complement activation (Rinder et al. (1995) J. Clin. Invest. 96:1564) or antibody-mediated complement activation (Biesecker (1989) J. Immunol. 142:2654). Matis and Rollins (supra) have developed C5-specific monoclonal antibodies as an anti-inflammatory biopharmaceutical.

C3 is an attractive target for the development of a Complement System inhibitor, as it is common to both pathways. Inhibition of C3 using recombinant versions of a natural inhibitors (Kalli et al. (1994) Springer Semin. Immunopathol. 15:417) can prevent cell-mediated tissue injury (Mulligan et al. (1992) J. Immunol. 148:1479) and this has been shown to have therapeutic benefit in diseases such as myocardial infarction (Weisman et al. (1990) Science 249:146) and liver ischemia/reperfusion (Chávez-Cartaya et al. (1995) Transplantation 59:1047). Controlling C3 limits most biological activities of the Complement System. Most natural inhibitors, including DAF, MCP, CR1 and Factor 14 target C3.

SELEX

A method for the in vitro evolution of Nucleic Acid molecules with highly specific binding to Target molecules has been developed. This method, Systematic Evolution of Ligands by EXponential Enrichment, termed the SELEX process, is described in U.S. patent application Ser. No. 07/536,428, filed Jun. 11, 1990, entitled "Systematic Evolution of Ligands by Exponential Enrichment," now abandoned; U.S. patent application Ser. No. 07/714,131, filed Jun. 10, 1991, entitled "Nucleic Acid Ligands," now U.S. Pat. No. 5,475,096; U.S. patent application Ser. No. 07/931, 473, filed Aug. 17, 1992, entitled "Methods for Identifying Nucleic Acid Ligands," now U.S. Pat. No. 5,270,163 (see also WO 91/19813), each of which is herein specifically incorporated by reference. Each of these applications, collectively referred to herein as the SELEX Patent Applications, describes a fundamentally novel method for making a Nucleic Acid Ligand to any desired Target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of Nucleic Acids, preferably comprising a segment of randomized sequence, the SELEX method includes steps of contacting the mixture with the Target under conditions favorable for binding, partitioning unbound Nucleic Acids from those Nucleic Acids which have bound specifically to Target molecules, dissociating the Nucleic Acid-Target complexes, amplifying the Nucleic Acids dissociated from the Nucleic Acid-Target complexes to yield a ligand-enriched mixture of Nucleic Acids, then reiterating the steps of binding, partitioning, dissociating and amplifying through as many cycles as desired to yield highly specific, high affinity Nucleic Acid Ligands to the Target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," abandoned in favor of U.S. patent application Ser. No. 08/198,670, now U.S. Pat. No. 5,707,796, describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands," now abandoned, describes a SELEX-based method for selecting Nucleic Acid Ligands containing photoreactive groups capable of binding and/or photocrosslinking to and/or photoinactivating a Target molecule. U.S. patent application Ser. No. 08/134,028, filed Oct. 7, 1993, entitled "High-Affinity Nucleic Acid Ligands That Discriminate Between Theophylline and Caffeine," abandoned in favor of U.S. patent application Ser. No. 08/443,957, now U.S. Pat. No. 5,580,737, describes a method for identifying highly specific Nucleic Acid Ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," abandoned in favor of U.S. patent application Ser. No. 08/461,069, now U.S. Pat. No. 5,567,588, and U.S. patent application Ser. No. 08/792,075, filed Jan. 31, 1997, entitled "Flow Cell SELEX," now U.S. Pat. No. 5,861,254, describe SELEX-based methods which achieve highly efficient partitioning between oligonucleotides having high and low affinity for a Target molecule. U.S. patent application Ser. No. 07/964,624, filed Oct. 21, 1992, entitled "Nucleic Acid Ligands to HIV-RT and HIV-1 Rev," now U.S. Pat. No. 5,496,938, describes methods for obtaining improved Nucleic Acid Ligands after the SELEX process has been performed. U.S. patent application Ser. No. 08/400,440, filed Mar. 8, 1995, entitled "Systematic Evolution of Ligands by EXponential Enrichment: Chemi-SELEX," now U.S. Pat. No. 5,705,337, describes methods for covalently linking a ligand to its Target.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now U.S. Pat. No. 5,660,985, that describes oligonucleotides containing nucleotide derivatives chemically modified at the 5- and 2'-positions of pyrimidines. U.S. patent application Ser. No. 08/134,028, now U.S. Pat. No. 5,580,737, supra, describes highly specific Nucleic Acid Ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2'-Modified Nucleosides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637,459 and U.S. patent application Ser. No. 08/234,997, filed Apr. 28, 1994, entitled "Systematic Evolution of Ligands by Exponential Enrichment: Blended SELEX," now U.S. Pat. No. 5,686,867, respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

BRIEF SUMMARY OF THE INVENTION

The present invention includes methods of identifying and producing Nuclcic Acid Ligands to Complement System Proteins and homologous proteins and the Nucleic Acid Ligands so identified and produced. By homologous proteins it is meant a degree of amino acid sequence identity of 80% or more. Exemplified herein is a method of identifying and producing Nucleic Acid Ligands to C1q, C3 and C5, and the Nucleic Acid Ligands so produced. Nucleic Acid Ligand sequences are provided that are capable of binding specifically to C1q, C3 and C5. In particular, RNA sequences are provided that are capable of binding specifically the C1q, C3 and C5. Specifically included in the invention are the RNA ligand sequences shown in Tables 2–6 (SEQ ID NOS:5–74 and 76–155). Also included in the invention are Nucleic Acid Ligands that inhibit the function of proteins of the Complement System. Specifically included in the invention herein are RNA ligands that inhibit the function of C1q, C3 and C5. Also included are Nucleic Acid Ligands that inhibit and/or activate the Complement System.

Further included in this invention is a method of identifying Nucleic Acid Ligands and Nucleic Acid Ligand sequences to Complement System Proteins comprising the steps of (a) preparing a Candidate Mixture of Nucleic Acids, (b) contacting the Candidate Mixture of Nucleic Acids with a Complement System Protein, (c) partitioning between members of said Candidate Mixture on the basis of affinity to said Complement System Protein, and (d) amplifying the selected molecules to yield a mixture of Nucleic Acids enriched for Nucleic Acid sequences with a relatively higher affinity for binding to said Complement System Protein.

Also included in this invention is a method of identifying Nucleic Acid Ligands and Nucleic Acid Ligand sequences to C1q, C3 and C5, comprising the steps of (a) preparing a Candidate Mixture of Nucleic Acids, (b) contacting the Candidate Mixture of Nucleic Acids with C1q, C3 or C5, (c) partitioning between members of said Candidate Mixture on the basis of affinity to C1q, C3 or C5, and (d) amplifying the selected molecules to yield a mixture of Nucleic Acids enriched for Nucleic Acid sequences with a relatively higher affinity for binding to C1q, C3 or C5.

More specifically, the present invention includes the RNA ligands to C1q, C3 and C5 identified according to the above-described method, including RNA ligands to C1q, including those ligands shown in Table 2 (SEQ ID NOS:5–20) and Table 6 (SEQ ID NOS:84–155), RNA ligands to C3, including those sequences shown in Table 3 (SEQ ID NOS:21–46), and RNA ligands to C5, including those sequences shown in Table 4 (SEQ ID NOS:47–74) and Table 5 (SEQ ID NOS:76–83). Also included are RNA ligands to C1q, C3 and C5 that are substantially homologous to any of the given ligands and that have substantially the same ability to bind C1q, C3 or C5, and inhibit the function of C1q, C3 or C5. Further included in this invention are Nucleic Acid Ligands to C1q, C3 and C5 that have substantially the same structural form as the ligands presented herein and that have substantially the same ability to bind C1q, C3 or C5 and inhibit the function of C1q, C3 or C5.

The present invention also includes modified nucleotide sequences based on the RNA ligands identified herein and mixtures of the same.

DETAILED DESCRIPTION OF THE INVENTION

Figure 1:
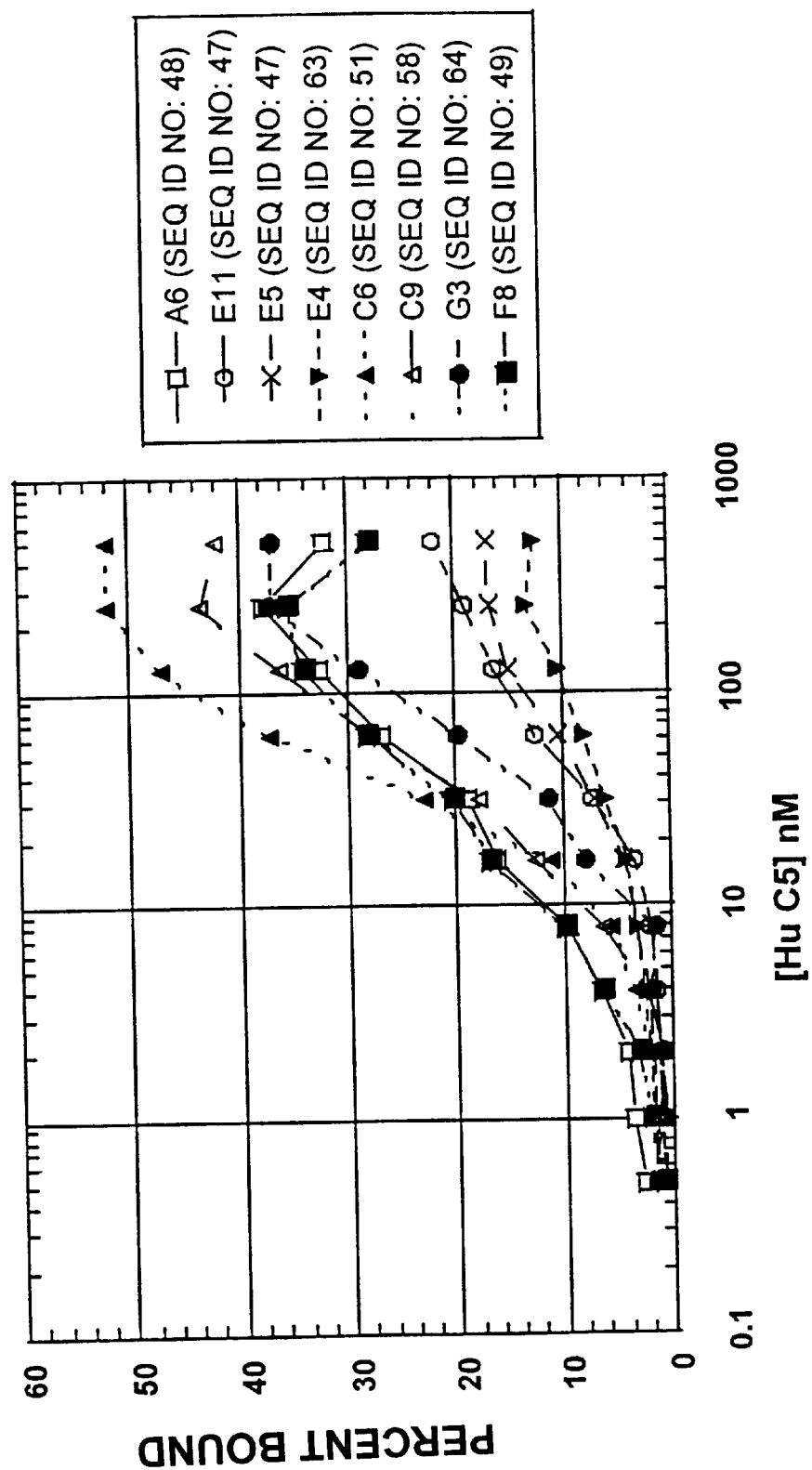
FIG. 1 shows binding curves for 2'-F RNA ligands A6 (SEQ ID NO:48) (□), E11(SEQ ID NO:47) (○), E5c (SEQ ID NO:47) (x), E4(SEQ ID NO:63) (▼), C6 (SEQ ID NO:51) (▲), C9 (SEQ ID NO:58) (Δ), G3 (SEQ ID NO:64) (●) and F8 (SEQ ID NO:49) (■), to human C5.

This application describes Nucleic Acid Ligands to Complement System Proteins identified generally according to the method known as SELEX. As stated earlier, the SELEX technology is described in detail in the SELEX Patent Applications which are incorporated herein by reference. Certain terms used to described the invention herein are defined as follows:

"Nucleic Acid Ligand" as used herein is a non-naturally occurring Nucleic Acid having a desirable action on a Target. A desirable action includes, but is not limited to, binding of the Target, catalytically changing the Target, reacting with the Target in a way which modifies/alters the Target or the functional activity of the Target, covalently attaching to the Target as in a suicide inhibitor, and facilitating the reaction between the Target and another molecule. In the preferred embodiment, the desirable action is specific binding to a Target molecule, such Target molecule being a three dimensional chemical structure other than a polynucleotide that binds to the Nucleic Acid Ligand through a mechanism which predominantly depends on Watson/Crick base pairing or triple helix binding, wherein the Nucleic Acid Ligand is not a Nucleic Acid having the known physiological function of being bound by the Target molecule. Nucleic Acid Ligands include Nucleic Acids that are identified from a Candidate Mixture of Nucleic Acids, said Nucleic Acid Ligand being a ligand of a given Target by the method comprising: a) contacting the Candidate Mixture with the Target, wherein Nucleic Acids having an increased affinity to the Target relative to the Candidate Mixture may be partitioned from the remainder of the Candidate Mixture; b) partitioning the increased affinity Nucleic Acids from the remainder of the Candidate Mixture; and c) amplifying the increased affinity Nucleic Acids to yield a ligand-enriched mixture of Nucleic Acids.

"Candidate Mixture" is a mixture of Nucleic Acids of differing sequence from which to select a desired ligand. The source of a Candidate Mixture can be from naturally-occurring Nucleic Acids or fragments thereof, chemically synthesized Nucleic Acids, enzymatically synthesized Nucleic Acids or Nucleic Acids made by a combination of the foregoing techniques. In a preferred embodiment, each Nucleic Acid has fixed sequences surrounding a randomized region to facilitate the amplification process. "Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"SELEX" methodology involves the combination of selection of Nucleic Acid Ligands which interact with a Target in a desirable manner, for example binding to a protein, with amplification of those selected Nucleic Acids. Iterative cycling of the selection/amplification steps allows selection of one or a small number of Nucleic Acids which interact most strongly with the Target from a pool which contains a very large number of Nucleic Acids. Cycling of the selection/amplification procedure is continued until a selected goal is achieved. In the present invention, the SELEX methodology is employed to obtain Nucleic Acid Ligands to C1q, C3 and C5. The SELEX methodology is described in the SELEX Patent Applications.

"Target" means any compound or molecule of interest for which a ligand is desired. A Target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the Target is a Complement System Protein, preferably C1q, C3 and C5.

"Complement System Protein" means any protein or component of the Complement System including, but not limited to, C1, C1q, CIr, CIs, C2, C3, C3a, C3b, C4, C4a, C5, C5a, C5b, C6, C7, C8, C9, Factor B (B), Factor D (D), Factor H (H), and receptors thereof, and other soluble and membrane inhibitors/control proteins.

"Complement System" is a set of plasma and membrane proteins that act together in a regulated cascade system to attack extracellular forms of pathogens or infected or transformed cells, and in clearance of immune reactants or cellular debris. The Complement System can be activated spontaneously on certain pathogens or by antibody binding to the pathogen. The pathogen becomes coated with Complement System Proteins (opsonized) for uptake and destruction. The pathogen can also be directly lysed and killed. Similar mechanisms target infected, transformed or damaged cells. The Complement System also participates in clearance of immune and cellular debris.

The SELEX process is described in U.S. patent application Ser. No. 07/536,428, filed Jun. 11, 1990, entitled "Systematic Evolution of Ligands by EXponential Enrichment," now abandoned; U.S. patent application Ser. No. 07/714,131, filed Jun. 10, 1991, entitled "Nucleic Acid Ligands," now U.S. Pat. No. 5,475,096; U.S. patent application Ser. No. 07/931,473, filed Aug. 17, 1992, entitled "Methods for Identifying Nucleic Acid Ligands," now U.S. Pat. No. 5,270,163, (see also WO 91/19813). These applications, each specifically incorporated herein by reference, are collectively called the SELEX Patent Applications.

In its most basic form, the SELEX process may be defined by the following series of steps:

1) A Candidate Mixture of Nucleic Acids of differing sequence is prepared. The Candidate Mixture generally includes regions of fixed sequences (i.e., each of the members of the Candidate Mixture contains the same sequences in the same location) and regions of randomized sequences. The fixed sequence regions are selected either: (a) to assist in the amplification steps described below, (b) to mimic a sequence known to bind to the Target, or (c) to enhance the concentration of a given structural arrangement of the Nucleic Acids in the Candidate Mixture. The randomized sequences can be totally randomized (i.e., the probability of finding a base at any position being one in four) or only partially randomized (e.g., the probability of finding a base at any location can be selected at any level between 0 and 100 percent).

2) The Candidate Mixture is contacted with the selected Target under conditions favorable for binding between the Target and members of the Candidate Mixture. Under these circumstances, the interaction between the Target and the Nucleic Acids of the Candidate Mixture can be considered as forming Nucleic Acid-Target pairs between the Target and those Nucleic Acids having the strongest affinity for the Target.

3) The Nucleic Acids with the highest affinity for the Target are partitioned from those Nucleic Acids with lesser affinity to the Target. Because only an extremely small number of sequences (and possibly only one molecule of Nucleic Acid) corresponding to the highest affinity Nucleic Acids exist in the Candidate Mixture, it is generally desirable to set the partitioning criteria so that a significant amount of the Nucleic Acids in the Candidate Mixture (approximately 5–50%) are retained during partitioning.

4) Those Nucleic Acids selected during partitioning as having the relatively higher affinity to the Target are then amplified to create a new Candidate Mixture that is enriched in Nucleic Acids having a relatively higher affinity for the Target.

5) By repeating the partitioning and amplifying steps above, the newly formed Candidate Mixture contains fewer and fewer weakly binding sequences, and the average degree of affinity of the Nucleic Acids to the Target will generally increase. Taken to its extreme, the SELEX process will yield a Candidate Mixture containing one or a small number of unique Nucleic Acids representing those Nucleic Acids from the original Candidate Mixture having the highest affinity to the Target molecule.

The SELEX Patent Applications describe and elaborate on this process in great detail. Included are Targets that can be used in the process; methods for partitioning Nucleic Acids within a Candidate Mixture; and methods for amplifying partitioned Nucleic Acids to generate enriched Candidate Mixture. The SELEX Patent Applications also describe ligands obtained to a number of target species, including both protein Targets where the protein is and is not a Nucleic Acid binding protein.

The SELEX method further encompasses combining selected Nucleic Acid Ligands with lipophilic or Non-Immunogenic, High Molecular Weight compounds in a diagnostic or therapeutic complex as described in U.S. patent application Ser. No. 08/434,465, filed May 4, 1995, entitled "Nucleic Acid Ligand Complexes, now U.S. Pat. No. 6,011,020," VEGF Nucleic Acid Ligands that are associated with a Lipophilic Compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes," now U.S. Pat. No. 5,859,228, VEGF Nucleic Acid Ligands that are associated with a Lipophilic Compound, such as a glycerol lipid, or a Non-Immunogenic, High Molecular Weight Compound, such as polyalkylene glycol, are further described in U.S. patent application Ser. No. 08/897,351, filed Jul. 21, 1997, entitled "Vascular Endothelial Growth Factor (VEGF) Nucleic Acid Ligand Complexes, now U.S. Pat. No. 6,051,698." VEGF Nucleic Acid Ligands that are associated with a Non-Immunogenic, High Molecular Weight compound or lipophilic compound are also further described in PCT/US97/18944, filed Oct. 17, 1997, entitled "Vascular Endothelial Growth Factor (VEGF) Nucleic Acid Ligand Complexes." Each of the above described patent applications which describe modifications of the basic SELEX procedure are specifically incorporated by reference herein in their entirety.

Certain embodiments of the present invention provide a complex comprising one or more Nucleic Acid Ligands to a Complement System Protein covalently linked with a Non-Immunogenic, High Molecular Weight compound or lipophilic compound. A complex as used herein describes the molecular entity formed by the covalent linking of the Nucleic Acid Ligand of a Complement System Protein to a Non-Immunogenic, High Molecular Weight compound. A Non-Immunogenic, High Molecular Weight compound is a compound between approximately 100 Da to 1,000,000 Da, more preferably approximately 1000 Da to 500,000 Da, and most preferably approximately 1000 Da to 200,000 Da, that typically does not generate an immunogenic response. For the purposes of this invention, an immunogenic response is one that causes the organism to make antibody proteins. In one preferred embodiment of the invention, the Non-Immunogenic, High Molecular Weight compound is a polyalkylene glycol. In the most preferred embodiment, the polyalkylene glycol is polyethylene glycol (PEG). More preferably, the PEG has a molecular weight of about 10–80K. Most preferably, the PEG has a molecular weight of about 20–45K. In certain embodiments of the invention, the Non-Immunogenic, High Molecular Weight compound can also be a Nucleic Acid Ligand.

Another embodiment of the invention is directed to complexes comprised of a Nucleic Acid Ligand to a Complement System Protein and a lipophilic compound. Lipophilic compounds are compounds that have the propensity to associate with or partition into lipid and/or other materials or phases with low dielectric constants, including structures that are comprised substantially of lipophilic components. Lipophilic compounds include lipids as well as non-lipid containing compounds that have the propensity to associate with lipid (and/or other materials or phases with low dielectric constants). Cholesterol, phospholipid, and glycerol lipids, such as dialkylglycerol, diacylglycerol, and glycerol amide lipids are further examples of lipophilic compounds. In a preferred embodiment, the lipophilic compound is a glycerol lipid.

The Non-Immunogenic, High Molecular Weight compound or lipophilic compound may be covalently bound to a variety of positions on the Nucleic Acid Ligand to a Complement System Protein, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the Nucleic Acid. In embodiments where the lipophilic compound is a glycerol lipid, or the Non-Immunogenic, High Molecular Weight compound is polyalkylene glycol or polyethylene glycol, preferably the Non-Immunogenic, High Molecular Weight compound is bonded to the 5' or 3' hydroxyl of the phosphate group thereof. In the most preferred embodiment, the lipophilic compound or Non-Immunogenic, High Molecular Weight compound is bonded to the 5' hydroxyl of the phosphate group of the Nucleic Acid Ligand. Attachment of the Non-Immunogenic, High Molecular Weight compound or lipophilic compound to the Nucleic Acid Ligand of the Complement System Protein can be done directly or with the utilization of linkers or spacers.

A linker is a molecular entity that connects two or more molecular entities through covalent bonds or non-covalent interactions, and can allow spatial separation of the molecular entities in a manner that preserves the functional properties of one or more of the molecular entities. A linker can also be known as a spacer.

The complex comprising a Nucleic Acid Ligand to a Complement System Protein and a Non-Immunogenic, High Molecular Weight compound or lipophilic compound can be further associated with a lipid construct. Lipid constructs are structures containing lipids, phospholipids, or derivatives thereof comprising a variety of different structural arrangements which lipids are known to adopt in aqueous suspension. These structures include, but are not limited to, lipid bilayer vesicles, micelles, liposomes, emulsions, lipid ribbons or sheets, and may be complexed with a variety of drugs and components which are known to be pharmaceutically acceptable. In the preferred embodiment, the lipid construct is a liposome. The preferred liposome is unilamellar and has a relative size less than 200 nm. Common additional components in lipid constructs include cholesterol and alpha-tocopherol, among others. The lipid constructs may be used alone or in any combination which one skilled in the art would appreciate to provide the characteristics desired for a particular application. In addition, the technical aspects of lipid constructs and liposome formation are well known in the art and any of the methods commonly practiced in the field may be used for the present invention.

The methods described herein and the Nucleic Acid Ligands identified by such methods are useful for both therapeutic and diagnostic purposes. Therapeutic uses include the treatment or prevention of diseases or medical conditions in human patients, specifically diseases or conditions caused by activation of the Complement System. The Complement System does not have to be the only cause of the disease state, but it may be one of several factors, each of which contributes to pathogenesis. Such diseases or conditions include, but are not limited to, renal diseases, such as lupus nephiltis and membranoproliferative glomerulonephritis (MPGN), membranous nephritis, IgA nephropathy; rheumatological diseases, such as rheumatoid arthritis, systemic lupus erythematosus (SLE), Behcet's syndrome, juvenile rheumatoid, Sjögren's syndrome and systemic sclerosis; neurological diseases, such as myasthenia gravis, multiple sclerosis, cerebral lupus, Guillain-Barré syndrome and Alzheimer's disease; dermatological diseases, such as Pemphigus/pemphigoid, phototoxic reactions, vasculitis and thermal burns; hematological diseases, such as paroxysmal nocturnal hemoglobinuria (PNH), hereditary erythroblastic multinuclearity with positive acidified serum lysis test (HEMPAS) and idiopathic thrombocytopenic purpura (ITP); biocompatibility/shock diseases, such as post-bypass syndrome, adult respiratory distress syndrome (ARDS), catheter reactions, anaphylaxis, transplant rejection, pre-eclampsia, hemodialysis and platelet storage; vascular/pulmonary diseases, such as atherosclerosis, myocardial infarction, stroke and reperfusion injury; allergies, such as anaphylaxis, asthma and skin reactions; infection, such as septic shock, viral infection and bacterial infection; and other conditions, such as atheroma, bowel inflammation, thyroiditis, infertility, paroxysmal nocturnal hemoglobinuria (PNH) and hemolytic anemia.

The Complement System can be inhibited at several points in the activation cascade by targeting different components. Inhibition of C1q would block the initiation by either antibody or non-antibody mechanisms. Antibodies activate C1q in many diseases including SLE, myasthenia gravis, and arthritis. Non-antibody Complement System activation occurs in many diseases including Alzheimer's disease, myocardial infarction and septic shock. Blocking C1q could prevent the complement-mediated tissue injury in these diseases.

The Complement can also be activated in the absence of antibodies directly at the C3 stage. Activating surfaces including bacteria, virus particles or damaged cells can trigger Complement System activation that does not require C1q. An inhibitor of C3 could prevent Complement System activation and damage in these situations.

In other instances the inhibition of C5 is most useful. Activation of the Complement System by either C1q or C3 mechanisms both lead to activation of C5, so that inhibition of C5 could prevent Complement System-mediated damage by either pathway. However, both C1q and C3 are important in normal defense against microorganisms and in clearance of immune components and damaged tissue, while C5 is mostly dispensable for this function. Therefore, C5 can be inhibited either for a short term or a long term and the protective role of Complement System would not be compromised, whereas long term inhibition of C1q or C3 is not desirable. Finally, the C5 fragments C5a and C5b directly cause the majority of tissue injury and disease associated with unwanted Complement System activation. Therefore, inhibition of C5 is the most direct way of producing therapeutic benefit.

In other instances, the activation of the Complement System is desirable in the treatment or prevention of diseases or medical conditions in human patients. For example, the activation of the Complement System is desirable in treating bacterial or viral infections and malignancies. In addition, the activation of the Complement System on T-cells prior to transplantation could prevent rejection of an organ or tissue by eliminating the T-cells that mediate the rejection.

Furthermore, Nucleic Acid Ligands that bind to cell surface Targets could be made more efficient by giving them the ability to activate the Complement System. Nucleic Acid binding would then both inhibit a Target function and also eliminate the cell, for example, by membrane attack complex lysis and cell clearance through opsonization. Nucleic Acid Ligands could activate the Complement System through either the classical or the alternative pathways. C1q Nucleic Acid Ligands can be conjugated to other structures that target a cell surface component. For example, C1q Nucleic Acid Ligands can be conjugated to antibodies to cell targets, cytokines, growth factors, or a ligand to a cell receptor. This would allow the C1q Nucleic Acid Ligands to multimerize on the targeted cell surface and activate the Complement System, thereby killing the cell.

The prototype classical pathway activators are immune aggregates, which activate the Complement System through binding to globular head groups on the C Iq component. Generally, binding of two or more Fc domains to C1q is required; pentameric IgM is an especially efficient activator. In contrast, Nucleic Acid Ligands can activate through binding at a separate site on the C1q collagen-like tail region. This site also binds to a variety of other non-antibody activators including C-reactive protein, serum amyloid protein, endotoxin, β-amyloid peptide 1–40 and mitochondrial membranes. As with immunoglobulin, these non-antibody activators need to be multimerized to activate.

Nucleic Acid Ligands that bind to sites on the collagen-like region of C1q may also become activators when aggregated. Such a Complement System-activating aggregate may be lytic if formed on a cell surface, such as binding to a tumor-specific antigen (TSA) or to a leukocyte antigen. The extent of Nucleic Acid Ligand-mediated activation increases with the extent of Nucleic Acid Ligand aggregation (i.e., multiplicity of Nucleic Acid Ligand-C1q interaction). The Complement System-mediated killing is especially specific if the Nucleic Acid Ligands circulate as monomers which do not activate, but become activators when they are multimerized on the targeted cell surface.

As with any Complement System activation, the extent and specificity is determined by the amount of C3 deposited onto the targeted cell. Deposited C3 forms an enzyme convertase that cleaves C5 and initiates membrane attack complex formation. C3 is also the classical serum opsonin for targeting phagocytic ingestion. The prototype alternative pathway activators are repeating carbohydrate units including bacterial and yeast cell walls, fucoidin and Sepharose, or glycolipids such as endotoxin or the glycocalyx. Nucleic Acid Ligands could activate the alternative pathway by aggregating the C3 component on the cell surface. Depositing C3 on a cell promotes Factor B binding and alternative pathway C3 convertase formation. Binding of a Nucleic Acid Ligand to C3 blocks binding of the inhibitor Factor H and prevents C3b decay. This would also increase C3 convertase formation and alternative path activation. Nucleic Acid Ligands to C3 may have this activity since heparin binds activated C3 and can promote alternative pathway activation. Binding of Nucleic Acid Ligands to C3 blocks binding to C3 of the membrane-associated inhibitors CR1, CR2, MCP and DAF, preventing C3b convertase decay and stimulating alternative pathway activation. This alternative pathway mechanism can be as efficient as C1q-dependent activation in cell killing and lysis.

Nucleic Acid Ligand-mediated Complement System cell killing could be employed in several ways, for example, by: a) direct killing of tumor cells; b) lysis of targeted microorganisms or infected cells; and c) elimination of lymphocytes or lymphocyte subsets. Nucleic Acid Ligands could replace antibodies currently used for these purposes.

Diagnostic utilization may include both in vivo or in vitro diagnostic applications. The SELEX method generally, and the specific adaptations of the SELEX method taught and claimed herein specifically, are particularly suited for diagnostic applications. The SELEX method identifies Nucleic Acid Ligands that are able to bind targets with high affinity and with surprising specificity. These characteristics are, of course, the desired properties one skilled in the art would seek in a diagnostic ligand.

The Nucleic Acid Ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any Nucleic Acid Ligand by procedures known in the art to incorporate a labeling tag in order to track the presence of such ligand. Such a tag could be used in a number of diagnostic procedures. The Nucleic Acid Ligands to C1q, C3 and C5 described herein may specifically be used for identification of the C1q, C3 or C5 protein.

The SELEX process provides high affinity ligands of a target molecule. This represents a singular achievement that is unprecedented in the field of Nucleic Acids research. The present invention applies the SELEX procedure to the specific target C1q, which is part of the first component (C1) of the classical pathway of Complement System activation, to the specific target C3, which is part of both the classical and alternative pathway, and to the specific target C5, which is part of the terminal pathway. In the Example section below, the experimental parameters used to isolate and identify the Nucleic Acid Ligands to C1q, C3 and C5 are described.

In order to produce Nucleic Acids desirable for use as a pharmaceutical, it is preferred that the Nucleic Acid Ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the Nucleic Acid Ligand have the highest possible affinity to the Target.

Pharmaceutical agents, which include, but are not limited to, small molecules, antisense oligonucleotides, nucleosides, and polypeptides can activate the Complement System in an undesirable manner. Nucleic Acid Ligands to Complement System Proteins could be used as a prophylactic by transiently inhibiting the Complement System, so that a pharmaceutical agent could be administered and achieve a therapeutically effective amount without eliciting the undesirable side effect of activating the Complement System.

In co-pending and commonly assigned U.S. patent application Ser. No. 07/964,624, filed Oct. 21, 1992 (the '624 Application), now U.S. Pat. No. 5,496,938, methods are described for obtaining improved Nucleic Acid Ligands after SELEX has been performed. The '624 Application, entitled "Nucleic Acid Ligands to HIV-RT and HIV-1 Rev," is specifically incorporated herein by reference.

In the present invention, SELEX experiments were performed in order to identify RNA with specific high affinity for C1q, C3 and C5 from a degenerate library containing 30 or 50 random positions (30N or 50N). This invention includes the specific RNA ligands to C1q shown in Table 2 (SEQ ID NOS:5–20) and Table 6 (SEQ ID NOS:84–155), identified by the method described in Examples 2 and 6, the specific RNA ligands to C3 shown in Table 3 (SEQ ID NOS:21–46), identified by method described in Example 3, and the specific RNA ligands to C5 shown in Table 4 (SEQ ID NOS:47–74) and Table 5 (SEQ ID NOS:76–83), identified by methods described in Example 4. This invention further includes RNA ligands to C1q, C3 and C5 which inhibit the function of C1q, C3 and C5. The scope of the ligands covered by this invention extends to all Nucleic Acid Ligands of C1q, C3 and C5, modified and unmodified, identified according to the SELEX procedure. More specifically, this invention includes Nucleic Acid sequences that are substantially homologous to the ligands shown in Tables 2–6 (SEQ ID NOS:5–74 and 76–155). By substantially homologous, it is meant a degree of primary sequence homology in excess of 70%, most preferably in excess of 80%, and even more preferably in excess of 90%, 95% or 99%. The percentage of homology as described herein is calculated as the percentage of nucleotides found in the smaller of the two sequences which align with identical nucleotide residues in the sequence being compared when 1 gap in a length of 10 nucleotides may be introduced to assist in that alignment. A review of the sequence homologies of the ligands of C1q shown in Table 2 (SEQ ID NOS:5–20) and Table 6 (SEQ ID NOS:84–155) shows that sequences with little or no primary homology may have substantially the same ability to bind C1q. Similarly, a review of the sequence homologies of the ligands of C3 shown in Table 3 (SEQ ID NOS:21–46) shows that sequences with little or no primary homology may have substantially the same ability to bind C3. Similarly, a review of the sequence homologies of the ligands of C5 shown in Table 4 (SEQ ID NOS:47–74) and Table 5 (SEQ ID NOS:76–83) shows that sequences with little or no primary homology may have substantially the same ability to bind C5. For these reasons, this invention also includes Nucleic Acid Ligands that have substantially the same structure and ability to bind C1q as the Nucleic Acid Ligands shown in Table 2 (SEQ ID NOS:5–20) and Table 6 (SEQ ID NOS:84–155), Nucleic Acid Ligands that have substantially the same structure and ability to bind C3 as the Nucleic Acid Ligands shown in Table 3 (SEQ ID NOS:21–46) and Nucleic Acid Ligands that have substantially the same structure and ability to bind C5 as the Nucleic Acid Ligands shown in Table 4 (SEQ ID NO:47–74) and Table 5 (SEQ ID NOS:76–83). Substantially the same ability to bind C1q, C3 or C5 means that the affinity is within one or two orders of magnitude of the affinity of the ligands described herein. It is well within the skill of those of ordinary skill in the art to determine whether a given sequence—substantially homologous to those specifically described herein—has substantially the same ability to bind C1q, C3 or C5.

The invention also includes Nucleic Acid Ligands that have substantially the same postulated structure or structural motifs. Substantially the same structure or structural motifs can be postulated by sequence alignment using the Zukerfold program (see Zucker (1989) Science 244:48–52). As would be known in the art, other computer programs can be used for predicting secondary structure and structural motifs. Substantially the same structure or structural motif of Nucleic Acid Ligands in solution or as a bound structure can also be postulated using NMR or other techniques as would be known in the art.

One potential problem encountered in the therapeutic, prophylactic, and in vivo diagnostic use of Nucleic Acids is that oligonucleotides in their phosphodiester form may be quickly degraded in body fluids by intracellular and extracellular enzymes such as endonucleases and exonucleases before the desired effect is manifest. Certain chemical modifications of the Nucleic Acid Ligand can be made to increase the in vivo stability of the Nucleic Acid Ligand or to enhance or to mediate the delivery of the Nucleic Acid Ligand. See, e.g., U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now U.S. Pat. No. 5,660,985 and U.S. patent application Ser. No. 08/434,465, filed May 4, 1995, entitled "Nucleic Acid Ligand Complexes," which are specifically incorporated herein by reference. Modifications of the Nucleic Acid Ligands contemplated in this invention include, but are not limited to, those which provide other chemical groups that incorporate additional charge, polarizability, hydrophobicity, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, unusual base-pairing combinations such as the isobases isocytidine and isoguanidine and the like. Modifications can also include 3' and 5' modifications such as capping.

Where the Nucleic Acid Ligands are derived by the SELEX method, the modifications can be pre- or post-SELEX modifications. Pre-SELEX modifications yield Nucleic Acid Ligands with both specificity for their SELEX Target and improved in vivo stability. Post-SELEX modifications made to 2'-OH Nucleic Acid Ligands can result in improved in vivo stability without adversely affecting the binding capacity of the Nucleic Acid Ligand. The preferred modifications of the Nucleic Acid Ligands of the subject invention are 5' and 3' phosphorothioate capping and/or 3'-3' inverted phosphodiester linkage at the 3' end. In one preferred embodiment, the preferred modification of the Nucleic Acid Ligand is a 3'-3' inverted phosphodiester linkage at the 3' end. Additional 2' fluoro (2'-F) and/or 2' amino (2'-NH$_2$) and/or 2' O methyl (2'-OMe) modification of some or all of the nucleotides is preferred. Described herein are Nucleic Acid Ligands that were 2'-NH$_2$ modified or 2'-F modified and incorporated into the SELEX process.

Other modifications are known to one of ordinary skill in the art. Such modifications may be made post-SELEX (modification of previously identified unmodified ligands) or by incorporation into the SELEX process.

As described above, because of their ability to selectively bind C1q, C3 and C5, the Nucleic Acid Ligands to C1q, C3 and C5 described herein are useful as pharmaceuticals. This invention, therefore, also includes a method for treating Complement System-mediated diseases by administration of a Nucleic Acid Ligand capable of binding to a Complement System Protein or homologous proteins. Certain diseases or conditions such as Alzheimer's disease or myocardial infarction activate C1q through the collagen-like region. In Alzheimer's disease, β-amyloid activates C1q. Structures in heart muscle that are exposed during myocardial infarction such as intermediate filaments, mitochondrial membranes or actin activate C1q. Nucleic Acid Ligands to C3 or to C5 could also inhibit Complement System activation in Alzheimer's disease or myocardial infarction, whether the Complement System is activated through C1q by antibody or non-antibody mechanisms, or independent of C1q through the alternative pathway. Thus, the Nucleic Acid Ligands of the present invention may be useful in treating Alzheimer's disease or myocardial infarction.

Therapeutic compositions of the Nucleic Acid Ligands may be administered parenterally by injection, although other effective administration forms, such as intraarticular injection, inhalant mists, orally active formulations, transdermal iontophoresis or suppositories are also envisioned. One preferred carrier is physiological saline solution, but it is contemplated that other pharmaceutically acceptable carriers may also be used. In one preferred embodiment, it is envisioned that the carrier and the Nucleic Acid Ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The maimer of administering formulations containing Nucleic Acid Ligands for systemic delivery may be via subcutaneous, intramuscular, intravenous, intranasal or vaginal or rectal suppository.

In the Examples that follow, the use of SELEX methodology to identify high affinity RNA ligands to C1q, C3 and C5 is described.

The following Examples are provided to explain and illustrate the present invention and are not intended to be limiting of the invention. Example 1 describes the various materials and experimental procedures used in Examples 2, 3, 4 and 6. Example 2 describes the generation of 2'-$NH_2$ RNA ligands to C1q. Example 3 describes the generation of 2'-F Nucleic Acid Ligands of Complement System Protein C3. Example 4 describes the generation of 2'-F Nucleic Acid Ligands of Complement System Protein C5. Example 5 describes the activation of the Complement System through C1q ligands. Example 6 describes the generation of 2'-F RNA ligands to C1q.

EXAMPLE 1

Experimental Procedures

This example provides general procedures followed and incorporated in Examples 2, 3, 4 and 6 for the identification of 2'-$NH_2$ and 2'-F RNA ligands to C1q, and 2'-F ligands to C3 and C5.

A. Biochemicals

C1q, C3, C5 and C4-deficient guinea pig sera were obtained from Quidel (San Diego, Calif.). Bovine serum albumin (BSA), rabbit anti-BSA, CRP, SAP and β-amyloid peptides 1-40 and 1-42 were obtained from Sigma (St. Louis, Mo.). Nucleotides GTP, ATP, and deoxynucleotides were obtained from Pharmacia (Uppsala, Sweden). Taq polymerase was obtained from Perkin-Elmer (Norwalk, Conn.). Modified nucleotides 2'-$NH_2$-CTP and 2'-$NH_2$-UTP, and 2'-F-CTP and 2'-F-UTP, were prepared as described in Jellinek et al. (1995) Biochem. 34:11363. Avian reverse transcriptase was obtained from Life Sciences (St. Petersburg, Fla.) and T7 RNA polymerase from USB (Cleveland, Ohio). Nitrocellulose filters were obtained from Millipore (Bedford, Mass.). All chemicals were the highest grade available.

B. RNA SELEX procedures

The SELEX procedure has been described in detail in the SELEX Patent Applications (see also Jellinek et al. (1995) Biochem. 34:11363; Jellinek et al. (1994) Biochem. 33:10450). Briefly, a DNA template was synthesized with a 5' fixed region containing the T7 promoter, followed by a 30N or a 50N stretch of random sequence, and then with a 3'-fixed region (Table 1; SEQ ID NOS: 1–2). For the initial round of SELEX, 1 nmole (~$10^{14}$ unique sequences) of RNA was in vitro transcribed by T7 polymerase (Milligan et al. (1987) Nucleic Acids Res. 12:785) using mixed GTP/ATP and 2'-$NH_2$-CTP/UTP or 2'-F-CTP/UTP nucleotides, and with the addition of α-[$^{32}$P]-ATP. For this and subsequent SELEX rounds, the RNA was purified by electrophoresis on 8% acrylamide gels with 7 M urea, 10 mM Tris-Borate, 2 mM EDTA, pH 8.3 running buffer. After autoradiography, the band containing labeled, modified RNA transcript was excised and frozen at −70° C., then 400 μl of 100 mM NaCl, 2 mM EDTA was added, the gel was mashed, and the slurry was spun through 2 cm of glass-wool (Rnase-free—Alltech Associates, Deerfield, Ill.) and two nitrocellulose filters. The RNA was precipitated by addition of ⅕ vol of 6.6 M $NH_4OAc$, pH 7.7, plus 2 vol of ethanol. The pellet was washed twice with 80% ethanol, and taken to dryness. The dry RNA pellet was dissolved in phosphate buffered saline (Sambrook et al. (1989) Molecular Cloning. A laboratory Manual. Cold Spring Harbor Laboratory, Cold Spring Harbor, N.Y.) containing 1 mM $MgCl_2$ (MgPBS).

For each round of SELEX, the RNA was incubated with C1q, C3 or C5 in MgPBS for 10 minutes at 37° C. Then the sample was filtered through a 43 mm nitrocellulose filter, and the filter was washed with 10 ml of MgPBS. For some rounds, the diluted RNA was pre-soaked with nitrocellulose filters overnight to reduce background. Four samples were run in parallel for most rounds with lesser amounts (chosen to be in suitable range to measure binding) of both RNA and C1q, C3 or C5 to measure binding $K_d$ for each sample. In addition, at each round, a sample of RNA was filtered without protein to determine background.

Filters were air-dried, sliced into strips, counted, and then extracted for 60 minutes at 37° C. with 400 μl of 1% SDS, 0.5 mg/ml Proteinase K (Boehringer Mamnleim, Indianapolis, Ind.), 1.5 mM DTT, 10 mM EDTA, 0.1M Tris, pH 7.5, with addition of 40 μg tRNA carrier. The aqueous RNA was extracted with phenol, phenol/chloroform (1:1), and chloroform and then precipitated following addition of $NH_4OAc$/EtOH as above. The RNA was reverse transcribed in a volume of 50 μl for between 1 hour and overnight. The DNA was PCR amplified with specific primers (Table 1; SEQ ID NOS:3–4) in a volume of 500 μl for 12–14 cycles, and then phenol/chloroform extracted and NaOAc/EtOH precipitated. The DNA pellet was taken up in $H_2O$, and an aliquot was T7 transcribed for the next round of SELEX.

C. Cloning

DNA from the 12$^{th}$ or the 14$^{th}$ round was PCR amplified with primers which also contained a ligation site to facilitate cloning. The DNA was cloned into a pUC9 vector, and colonies were picked for overnight growth and plasmid mini-preps (PERFECTprep, 5'-3', Boulder, Colo.). The purified plasmids were PCR amplified with original 3' and 5' primers (as above), and products were analyzed by agarose gel electrophoresis (Sambrook et al. (1989) Molecular Cloning. A laboratory Manual, Cold Spring Harbor Laboratory, Cold Spring Harbor, N.Y.). DNA was T7 transcribed with α-[$^{32}$P]-ATP to prepare radiolabeled RNA for binding analysis and without radiolabel to prepare RNA for inhibition studies.

D. Sequencing

Plasmids purified using the PERFECTprep kit were sequenced with ABI dRhodamine Terminator cycling kit (Perkin-Elmer). Samples were sequenced on the ABI Prism 377 DNA Sequencer.

E. Binding Assays

Individual cloned DNA was T7 transcribed with α-[$^{32}$P]-ATP and the full length [$^{32}$P]-2'-NH$_2$-RNA or 2'-F-RNA was gel-purified (as above). RNA was suspended at approximately 5,000 cpm per 30 µl sample (<10 pM), and aliquots were incubated with various concentrations of C1q, C3 or C5 in MgPBS for 10 minutes at 37° C. Samples were then filtered through nitrocellulose, the filters washed with buffer and dried under an infrared lamp, and counted with addition of scintillation fluid (Ecoscint A, National Diagnostics, Atlanta, Ga.). A background sample of RNA alone was run in parallel. To measure inhibition of ligand binding to C1q, the RNA Nucleic Acid Ligand plus C1q plus inhibitor (e.g., the A-chain residue 14–26 site, SAP, β-amyloid peptide, CRP) were incubated for 10 minutes at 37° C., and then filtered. Filters were washed and counted.

RNA ligand binding to C1q was also measured in the presence of immune-complexes, which would block the binding of ligands to C1q head-groups. Immune complexes (IC) were formed by mixing 620 µg BSA at equivalence with 1 ml of rabbit anti-BSA (Sigma, St. Louis, Mo.) plus PEG 8000 added to 1% final concentration, and then the samples were incubated overnight at 4° C. The IC were pelleted by microfugation at 12,000 rpm for 10 minutes, washed five times with PBS, and suspended in 1 ml of MgPBS. For measurement of C1q RNA clone binding to C1q-immune complexes (C1q-IC), 20 µul of the purified [$^{32}$P]-RNA plus 20 µl of the IC were mixed with 20 µl of C1q at various concentrations at between $10^{-11}$ and $10^{-7}$ M in MgPBS plus 1% Triton. Samples were incubated for 30 minutes at room temperature, microfuged, and the pellets and supernatants counted.

F. Hemolytic Assays

Complement System consumption was measured by C4 hemolytic assay as described (Gaither et al. (1974) J. Immunol. 113:574). All samples were diluted and the assay run in veronal-buffered saline containing calcium, magnesium and 1% gelatin (GVB$^{++}$-complement buffer). For measurement of C4 consumption by β-amyloid peptide consumption, the peptide was added at 250 µg/ml to a 1/8 dilution of whole human serum and then incubated for 60 minutes at 37° C. The sample was then diluted for assay of C4 hemolytic activity. For assay of inhibition of β-amyloid peptide mediated complement consumption by C1q 2'-NH$_2$-RNA clones, the C1q RNA Nucleic Acid Ligand was included in the initial β-amyloid peptide-whole human serum incubation mixture, and then C4 amounts assayed as above.

Complement System inhibition by C5 Nucleic Acid Ligands was measured using human serum and antibody-coated sheep red blood cells. The red blood cells were incubated with a 1:40 dilution of fresh human serum and with serial dilutions of C5 ligand for 30 minutes at 37° C. Dilutions of serum and ligand were made in complement buffer (see previous paragraph). After incubation the samples were then diluted with 4° C. buffer containing EDTA to stop the reaction, and the hemoglobin release was quantitated from the optical density at 412 nm.

EXAMPLE 2

2'-NH$_2$ RNA Ligands To C1q

A. RNA SELEX

The pool of random 50N7-2'-NH, RNA bound to C1q by nitrocellulose filter assay with a $K_d$ of 2.3 µM. For SELEX round 1, the C1q concentration was between 0.156–1.25 µM and the RNA concentration was 15 µM. Throughout the SELEX process, the RNA concentrations were maintained at approximately 10-fold greater than the concentration of C1q, which was reduced at each round with a final round 14 C1q concentration of 136 pM. Background binding of RNA to nitrocellulose filters remained low throughout the SELEX procedure, in part because RNA was pre-adsorbed with nitrocellulose filters. The binding of pool RNA to C1q improved at each round. The evolved round 14 pool 2'-NH$_2$-RNA bound C1q with a $K_d$=670 pM, yielding an overall improvement in binding $K_d$ of 3400-fold.

Bulk RNA was then cloned for sequence determination and evaluation of binding. Through comparison of binding at 0.1 and 0.5 nM C1q, individual clones were ranked, and clones with C1q binding above background were sequenced and are shown in Table 2 (SEQ ID NOS:5–20). Family I contained 12 of the 19 total sequences. Family 2 contained three sequences. Both Family 3 and Family 4 contained two sequences. Both Family 1 and Family 2 sequences contain G-rich regions, and both have the repeated sequence motifs GGAG and GGUG. The identity and homology of Family 1 members is greatest in the 5' half, which is G-rich. The C-rich 3' half has only short stretches of sequence homology, and these are shown only with inclusion of large gap regions. Sequences from all families can be folded to give stem-loop structures with extensive Watson-Crick base-pairing. Full binding curves for the highest affinity ligands yielded a Kd range from 290 pM to 3.9 nM; the high affinity ligands were found in all four sequence families. All of the binding curves were monophasic. The binding maximum is not 100% because of variable amounts of nucleic acid alterations taking place during purification. This is known because usually ligands can be bound to protein, extracted, and then re-bound, and give maximum binding approaching 100% (data not shown).

B. Competition

2'-NHn-RNA ligands from different families interact with the same or overlapping sites on C1q, as shown by cross-competition. This site is on the collagen-like region, at or near the A-chain 14–26 residue site (Jiang et al. (1994) J. Immunol. 152:5050) as shown by two lines of evidence. First, C1q when bound to IC still binds the ligand #50 (SEQ ID NO:12); binding to immunoglobulin Fe would block the head region, but leave the collagen-like tail available, suggesting that SELEX ligands are bound to the tail. Second, and more direct, ligand #50 is competed by proteins which are known to bind the A-chain residue 14–26 site, including SAP, β-amyloid peptide, and CRP. Finally, ligand #50 is competed by a peptide that has the same amino acid sequence as residues 14–26 on the A-chain. This result is further supported by results for hemolytic inhibition as described below.

C. Consumption

SELEX ligand binding to the A-chain 14–26 amino acid site could activate C1q, or, alternatively, SELEX ligands could inhibit the binding of other molecules and prevent C1q activation. This was tested by measuring C4 consumption in serum after incubation with a 2'-NH$_2$ SELEX ligand, or after incubation with a known C1q activator together with a 2'-NH$_2$-SELEX ligand. The SELEX ligands when incubated in serum do not consume C4, and thus are not C1q activators. Nor do these ligands at this concentration inhibit serum lysis of antibody-coated sheep erythrocytes, which would occur if ligands bound near the C1q head groups (data not shown). The ligands do inhibit C4 consumption by another C1q activator, the β-amyloid 1-40 peptide. This peptide is known to activate C1q through binding at the A-chain 14-26 residue site; therefore, this inhibition confirms that SELEX ligands binds at this A-chain site. Control ligands from the SELEX process that did not bind C1q by nitrocellulose assay, were also ineffective in blocking the β-amyloid 1–40 peptide C1q activation.

EXAMPLE 3
2'-Fluoro Nucleic Acid Ligands of Complement System Protein C3

In order to generate ligands to complement protein C3, a library of about $10^{14}$ RNA was generated that contained 30 nucleotides of contiguous random sequence flanked by defined sequences. In this experiment, 30N random nucleotides of the initial Candidate Mixture were comprised of 2'-F pyrimidine bases. The rounds of selection and amplification were carried out as described supra in Example 1 using art-known techniques. In round 1 the 30N7-2'-F-RNA and C3 were both incubated at 3 μM. There was barely detectable binding at this round. Both the RNA and C3 concentrations were decreased during the SELEX procedure. Sequences derived from the SELEX procedure are shown in Table 3 (SEQ ID NOS:21–46).

EXAMPLE 4
2'-Fluoro Nucleic Acid Ligands of Complement System Protein C5

In order to generate ligands to human complement protein C5, a library of about $10^{14}$ RNA was generated that contained 30 nucleotides of contiguous random sequence flanked by defined sequences. In this experiment, the 30N random nucleotides of the initial Candidate Mixture were comprised of 2'-F pyrimidine bases. The rounds of selection and amplification were carried out as described supra in Example 1 using art-known techniques. In round 1 the 30N7-2'-F-RNA and C5 were both incubated at 3 μM. There was barely detectable binding at this round. Both the RNA and C5 concentrations were decreased during the SELEX procedure. Sequences derived from the SELEX procedure are shown in Table 4 (SEQ ID NOS:47–74). Sequences are placed into Group I or Group II. Binding of Nucleic Acid Ligands to human C5 from both groups are similar and are shown in FIG. 1. The Nucleic Acid Ligands bound to human C5 with a $K_d$ of between 6–20 nM.

Figure 2:
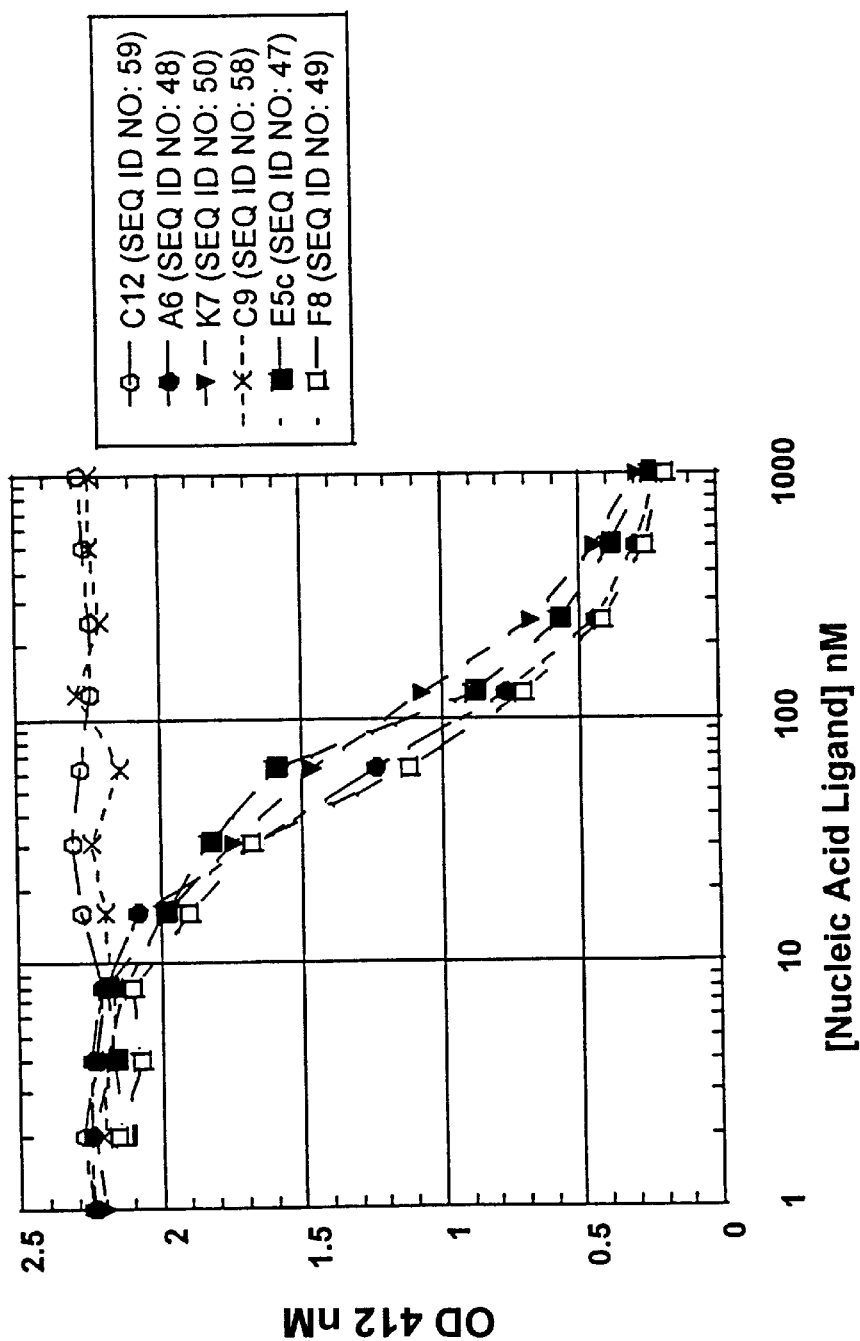
FIG. 2 shows the results of an inhibition assay in which 2'-F RNA ligands C12 (SEQ ID NO:59) (○), A6 (SEQ ID NO:48) (●), K7 (SEQ ID NO:50) (▼), C9 (SEQ ID NO:58) (x), E5c (SEQ ID NO:47) (■) and F8 (SEQ ID NO:49) (0) to human C5 were incubated with antibody-coated sheep erythrocytes and whole human serum. The results are presented as OD's versus concentration of ligand in nM.

The Nucleic Acid Ligands were assayed for inhibition of C5 activity. In this assay were mixed: a) antibody-coated sheep erythrocytes; b) whole human serum at a final dilution of 1:40; and c) dilutions of the purified Nucleic Acid Ligand. Samples were incubated at 37° C. for 30 minutes. Samples were then centrifuged to pellet the erythrocytes, and from the optical density at 412 nm the hemoglobin released into the supernatant through complement lysis was measured. This measurement gave the total Complement hemolytic activity and the inhibition by the Nucleic Acid Ligand of this total Complement hemolytic activity. The C5 Group I Nucleic Acid Ligands were able to totally inhibit Complement System activity as shown in FIG. 2.

Figure 3:
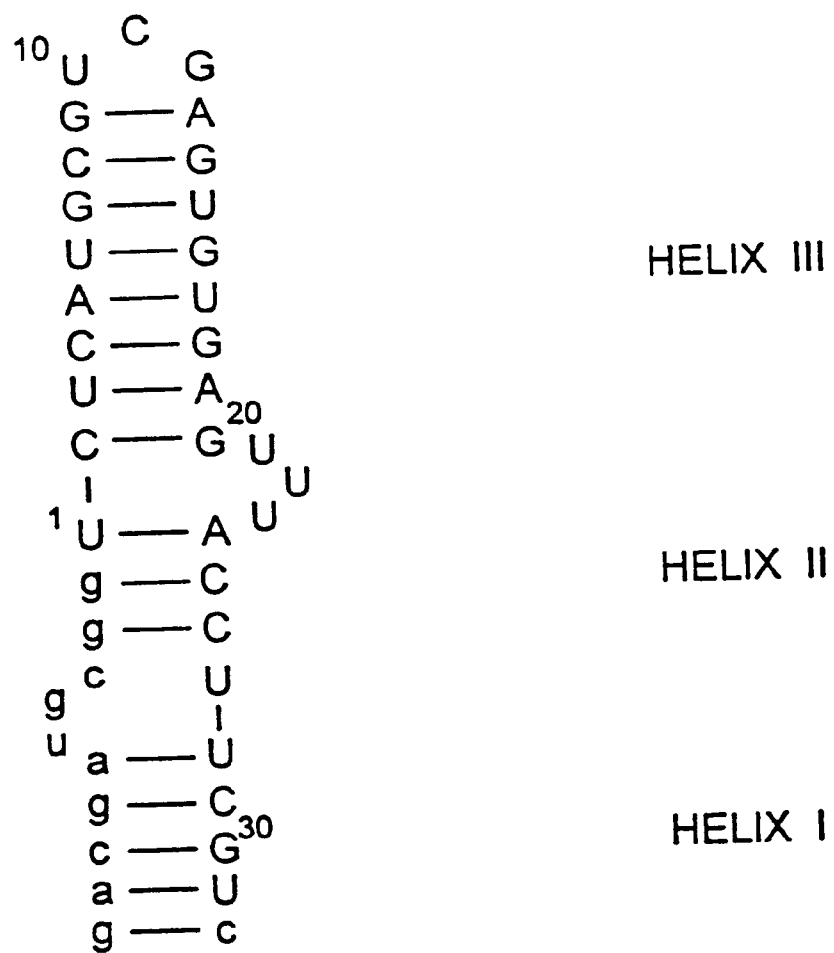
FIG. 3 shows a proposed secondary structure of truncated ligand (SEQ ID NO:75) to human C5.

A secondary structure for an inhibitory C5 Nucleic Acid Ligand as determined by current art (Green et al. (1995) Chem & Biol. 2:683) is shown in FIG. 3 (SEQ ID NO:75). The smallest structure which would bind C5 is determined by: a) radiolabeling the C5 Nucleic Acid Ligand at both the 3' and the 5' end; b) treating the labeled Nucleic Acid Ligand by partial base-hydrolyzed to split a portion of the bonds between nucleotides; c) incubating the partially hydrolyzed Nucleic Acid Ligand with C5 protein and then eluting the bound Nucleic Acid Ligand; and d) analyzing the eluted Nucleic Acid Ligand on gels. In this procedure, the Nucleic Acid Ligand initially binds to C5 as bases are removed from the Nucleic Acid Ligand. When an essential base is removed, the Nucleic Acid Ligand is no longer able to bind. This first essential base determines the boundary of the minimal Nucleic Acid Ligand structure. For a human C5 Nucleic Acid Ligand the smallest binding structure is believed to comprise the sequence with proposed base-pairing pattern shown in FIG. 3. The 38mer structure shown in FIG. 3 (SEQ ID NO:75) both binds to human C5 and inhibits total hemolytic complement activity, and thus possesses the characteristics required for a therapeutic molecule.

Human C5 Nucleic Acid Ligands can be tested for Complement activation in primate disease models. Also, Nucleic Acid Ligands to animal C5 can be tested for complement activation in animal models. For use in rat disease models, 2'-F Nucleic Acid Ligands to rat C5 were obtained as described above. The sequences of these Nucleic Acid Ligands are shown in Table 5 (SEQ ID NOS:76–83). Sequences are grouped into Family I, Family II and Family III. Members of all three families bind with similar affinity to rat C5. Nucleic Acid Ligands from each family were also assayed for inhibition of rat Complement System activity. Nucleic Acid Ligands from Family I and Family III inhibited rat complement, whereas a Nucleic Acid Ligand from Family II did not. An inhibitory Nucleic Acid Ligand can be used to inhibit Complement System activity in various rat disease models including, but not limited to, myasthenia gravis, myocardial infarction, glomerulonephritis, ARDS, arthritis and transplantation.

EXAMPLE 5
Activation of the Complement System through C1g Nucleic Acid Ligands Oligonucleotides can activate both classical and alternative pathways. Particularly, poly-G oligonucleotides which can form G-quartet structures and can interact with the C1q collagen-like region are able to form high molecular weight aggregates, which both bind and activate C1q. Phosphorothioate oligonucleotides, which have increased non-specific binding as compared with phosphodiester oligonucleotides, are also efficient Complement System activators, particularly poly-G containing phosphorothioate oligonucleotides. Results for oligonucleotide activation of solution phase Complement are shown below where classical pathway activation is measure by the release of C4d fragment by ELISA (Quidel, San Diego, Calif.), and alternative pathway activation is measure by Bb ELISA (Quidel, San Diego, Calif.). Although these pathways are separate, there is evidence to suggest that oligonucleotide activation of both pathways is C1q dependent.

| Sample | | [4d] μg (Class.) | [Bb] μg (Altern.) |
| --- | --- | --- | --- |
| Poly-AG | Random Co-Polymer | 8.1 | 18.9 |
| Poly-G | Random Co-Polymer | 1.2 | 29.3 |
| Poly-I | Random Co-Polymer | 0 | 14.7 |
| Poly-A | Random Co-Polymer | 0 | 0 |
| Poly-U | Random Co-Polymer | 0 | 1.8 |
| Poly-C | Random Co-Polymer | 0 | 2.5 |

-continued

| Sample | | [4d] μg (Class.) | [Bb] μg (Altern.) |
|---|---|---|---|
| Phosphorothioate Oligonucleotides | | | |
| GGCGGGGCTACGTACCGG-GGCTTTGTAAAACCCCGCC SEQ ID NO:156 | | −7.1 | 32.4 |
| CTCTCGCACCCATCTCTCTCCTTCT SEQ ID NO:157 | | 0.0 | 3.9 |
| BSA-anti-BSA | Immune Complexes | 8.0 | 11.9 |
| β-Amyloid Peptide | | 2.7 | n/d |
| Fucoidan | Sulfated Carbohydrate | | 27 |
| buffer | | 0.0 | 0.0 |

Complement System activation is also initiated on the erythrocyte membrane and is tested by hemolytic assays. Known activators, including 2'-OH poly-G and phosphorothioate oligonucleotides, as well as potential activators such as multimerized C1q Nucleic Acid Ligands and small (e.g., 15-mer) 2'-F poly-G oligonucleotides are coated on sheep erythrocytes and subsequent lysis of the erythrocytes by serum complement is measured. Methods of coating oligonucleotides and Nucleic Acid Ligands on cells include passive adsorption, chemical conjugation, streptavidin-biotin coupling, and specific Nucleic Acid binding. Following treatment with fresh rat or human serum, the deposition of complement components on the cell, membrane damage and lysis are measured by standard methods as would be known by one of skill in the art.

A. Aggregation of C1q Nucleic Acid Ligands

C1q Nucleic Acid Ligands are dimerized using chemical cross-linkers of various lengths. Alternatively, Nucleic Acid Ligand monomers are biotinylated and then multimerized with streptavidin. Each of these multimers are tested for complement activation and lysis of erythrocytes.

The addition of poly-G sequence to C1q Nucleic Acid Ligands provides additional binding ability and increases the ability of the oligonucleotide to activate the Complement System. In addition, short poly-G sequences on individual C1q Nucleic Acid Ligands can interact to form higher order structures, which serve to multimerize the C1q Nucleic Acid Ligands and cause activation.

B. Lysis of Erythrocytes and Leukocytes

Nucleic Acid Ligands that promote erythrocyte lysis are tested on nucleated cells, including lymphocytes and tumor cells. Nucleated cells have mechanisms of complement resistance that erythrocytes lack. For example, nucleated cells can shed antigens, bleb off membrane vesicles containing the complement components, and express increased levels of complement inhibitors as compared with erythrocytes and may up-regulate protective mechanisms upon initial complement attack. As high levels of activation are important for cell killing, activators are compared for amount of Complement System component deposition and extent of membrane damage. Also, different types and sources of tumor cells and lymphocytes are tested to determine if susceptibility is cell-type specific.

Nucleic Acid Ligands can be generated for virtually any target as described in the SELEX Patent Applications. Nucleic Acid Ligands to L-Selectin have been generated (See U.S. patent application Ser. No. 08/479,724, filed June 7, 1995, entitled "High Affinity Nucleic Acid Ligands to Lectins," which is incorporated herein by reference in its entirety). The diversity of lectin mediated functions provides a vast array of potential therapeutic targets for lectin antagonist. For example, antagonists to the mammalian selecting, a family of endogenous carbohydrate binding lectins, may have therapeutic applications in a variety of leukocyte-mediated disease states. Inhibition of selectin binding to its receptor blocks cellular adhesion and consequently may be useful in treating inflammation, coagulation, transplant rejection, tumor metastasis, rheumatoid arthritis, reperfusion injury, stroke, myocardial infarction, burns, psoriasis, multiple sclerosis, bacterial sepsis, hypovolaemic and traumatic shock, acute lung injury and ARDS. The coupling of C1q Nucleic Acid Ligands to L-Selectin Nucleic Acid Ligands makes the L-Selectin Nucleic Acid Ligand more efficient by promoting cell killing at the target. C1q Nucleic Acid Ligands are coupled to L-Selectin Nucleic Acid Ligands, and the conjugates are tested for leukocyte lysis as described above. Also, Nucleic Acid Ligands to other cell surface targets, antibodies to all targets that do not themselves activate complement, cytokines, growth factors, or a ligand to a cell receptor could be coupled to a C1q Nucleic Acid Ligand and used for cell killing.

C. In Vivo Testing of Complement Activation

Nucleic Acid Ligand-mediated Complement System activation is tested in animals to evaluate in vivo Nucleic Acid Ligand action. Erythrocytes and/or lymphocytes are coated with Nucleic Acid Ligands and injected into rats to test cell killing and lysis in vivo. Activating Nucleic Acid Ligands are also coupled to a MoAb that does not activate the Complement System, where the antibody is directed against a rat cell antigen (e.g., lymphocyte antigen). These calls are then coated with the Nucleic Acid Ligand-antibody conjugate and injected into rats. Alternatively, the Nucleic Acid Ligand-antibody conjugate is injected directly into the rat and then in vivo leukocyte killing is measured.

It is also possible that C1q Nucleic Acid Ligands cross-react with non-human C1q, and non-human C1q could be used for in vivo assays. C1q Nucleic Acid Ligands are tested against species such as mouse, rat and rabbit C1q. C1q is purified from serum and cross-reactivity with C1q Nucleic Acid Ligands is tested by nitrocellulose binding assay. Alternatively, C1q is bound to immune complexes which are added to serum and then C1q Nucleic Acid Ligand binding to the aggregate is tested. If Nucleic Acid Ligands are species-specific, then rat serum is depleted of rat C1q by continuous perfusion over a Ig-Sepharose column, and the serum is reconstituted with human C1q by methods known to one of skill in the art. These reconstituted animals are then used to test C1q Nucleic Acid Ligands for targeted Complement System activation and cell killing.

EXAMPLE 6

2'-Fluoro RNA Ligands to C1q

A. RNA SELEX

The pool of random 30N7-2'-F-RNA bound to C1q by nitrocellulose filter assay with a $K_d$ of 2.3 μM. For SELEX round 1, the C1q concentration was between 0.156–1.25 μM and the RNA concentration was 15 μM. Throughout the SELEX process, the RNA concentrations were maintained at approximately 10-fold greater than the concentration of C1q, which was reduced at each round with a final round 14 C1q concentration of 136 pM. Background binding of RNA to nitrocellulose filters remained low throughout the SELEX procedure, in part because RNA was pre-adsorbed with nitrocellulose filters. The binding of pool RNA to C1q improved at each round. The evolved round 14 pool 2'-F RNA bound C1q with a $K_d$ of 2nM, yielding an overall improvement in binding $K_d$ of 1–3000-fold.

Bulk RNA was then cloned for sequence determination and evaluation of binding. Through comparison of binding at 0.1 and 0.5 nM C1q, individual clones were ranked for binding affinity. Sequences of 2'-F-RNA are shown in Table 6 (SEQ ID NOS:84–155). The 2'-F-RNA sequences are not easily grouped into families, but these sequences are G-rich and are similar but not homologous with the 2'-NH$_2$-RNA sequences described in Example 2.

TABLE 1

| SEQ ID NO: | For RNA SELEX: |
|---|---|
|  | Synthetic DNA Template: |
| 1 | 5'-TAATACGACTCACTATAGGGAGGACGATGCGG-[N]$_{50}$-CAGACGACTCGCCCGA-3' |
|  | Starting random sequence RNA pool: |
| 2 | 5'-GGGAGGACGAUGCGG-[N]$_{50}$-CAGACGACUCGCCCGA-3' |
|  | Primer Set: |
| 3 | 5'-PRIMER: 5'-TAATACGACTCACTATAGGGAGGACGATGCGG-3' |
| 4 | 3'-PRIMER: 5'-TCGGGCGAGTCGTCTG-3' |

TABLE 2

2'-NH$_2$ RNA Ligands of Complement System Protein C1q*

| Clone No. | | SEQ ID NO: | Kd(nM) |
|---|---|---|---|
| Family 1 | | | |
| 3 | gggaggacgaugcggGAGGAGUGGAGGUAAACAAUAGGUCGGUAGCGACUCCCACUAACAGGCCUcagacgacucgcccga | 5 | |
| 12 | gggaggacgaugcggGUGGAGUGGAGGUAAACAAUAGGUCGGUAGCGACUCCCAGUAACGGCCUcagacgacucgcccga | 6 | |
| 23c | gggaggacgaugcaaGUGGAGUGGAGGUAUAACGGCCGGUAGGCAUCCCACUCGGGCCUAGCUcagacgaccgcccga | 7 | |
| 30 | gggaggacgaugcggGUGGAGUGGGGAUCAUACGGCUGGUAGCACGAGCUCCCUAACAGCGGUcagacgacucgcccga | 8 | |
| 36 | gggaggacgaugcggGAGGAGUGGAGGUAAACAAUAGGCCGUAGCCACUAACAGCCUcagagcgacucgcccga | 9 | 0.29 |
| 45 | gggaggacgaugcggUGGAGUGGAGGUAUACCGGCCGGUAGCGCAUCCCACUCGGGUCUGUGCUcagacgacucgcccga | 10 | 1.38 |
| 47 | gggaggacgaugcggGUGGAGCGGAGGUUUAUACGGCUGGUAGCUCGAGCUCCCUAACACGCGGUagacgacucgcccga | 11 | |
| 50 | gggaggacgaugcggGUGGAGUGGAGGUAUAACGGCCGGUAGCGCAUCCCACUCGGGUCUGUGCUagacgacucgcccga | 12 | 0.979 |
| 78 | gggaggacgaugcggGUGGAGUGGAGGGUAAACAAUGGCUGGUGGCAUUCGGAAUCUCCCAACGUagacgacucgcccga | 13 | |
| Family 2 | | | |
| 33 | gggaggacgaugcggGUUGCUGGUAGCCUGAUGUGGGUGGAGUGAGUGGAGGGUUGAAAAAUGcagacgacucgcccga | 14 | 3.85 |
| 40 | gggaggacgaugcggCUGGUAGCAUGUGCAUUGAUGGGAGGAGUGGAGGUCACCGUCAACCGUcagacgacucgcccga | 15 | |
| 43 | gggaggacgaugcggUUUCUCGGCCAGUAGUUUGCGGGUGGAGUGGAGGUAUAUCUGCGUCCUCGcagacgacucgcccga | 16 | |
| Family 3 | | | |
| 14 | gggaggacgaugcggCACCUCACCCCAUAUUGCCGGUUAUCGCGUAGGGUGAGCCCAGACACGAcagacgacucgcccga | 17 | 2.4 |
| 23 | gggaggacgaugcggCACUCACCUUCAUAUUGGCCGCCAUCCCCAGGGUUGAGCCCAGACACAGcagacgacucgcccga | 18 | 23 |
| Family 4 | | | |
| 22 | gggaggacgaugcggGCAUAGUGGGCAUCCCAGGGUUGCCUAACGGCAUCCGGGGUUGUUAUUGGcagacgacucgcccga | 19 | |
| 67 | gggaggacgaugcggCAGACGACUCGCCCGAGGGGAUCCCCCGGGCCUGCAGGAAUUCGAUAUcagacgacucgcccga | 20 | |

*Lower case letters represent the fixed region.

TABLE 3

Human C3 2'F-RNA sequences*

| Clone No. | | | | SEQ ID NO: |
|---|---|---|---|---|
| C3c 10 | gggaggacgaugcgg | AACUCAAUGGGCCUACUUUUUCCGUGGUCCU | cagacgacucgcccga | 21 |
| C3C 16 | gggaggacgaugcgg | AACUCAAUGGGCCUACUUUUUCCGUGGUCCU | cagacgacucgcccga | 22 |
| C3C 186 | gggaggacgaugcgg | AACUCAAUGGGCCGACUUUUUCCGUGUCCU | cagacgacucgcccg | 23 |
| C3C 162 | gggaggacgaugcgg | AACUCAAUGGGCCGACUUUCCGUGGUCCU | cagacgacucgcccga | 24 |
| C3C 141 | gggaggacgaugcgg | AACUCAAUGGGCNUACUUUUCCGUGGUCCU | cagacgacucgcccga | 25 |
| C3c 32 | gggaggacgaugcgg | AACUCAAUGGGCCGACUUUUCCGUGGUCCU | cagacgacucgcccga | 26 |
| 27C3B143 | gggaggacgaugcgg | AACUCAAUGGGCCGACUUUUUCCGUGGUCCU | cagacgacucgcccga | 27 |
| 30C3B149 | gggaggacgaugcgg | ACGCAGGGGAUGCUCACUUUGACUUUAGGC | cagacgacucgcccg | 28 |
| c3a 29c | gggaggacgaugcgg | ACUCGGCAUUCACUAACUUUUGCGCUCGU | cagacgacucgcccga | 29 |
| C3B 25 | gggaggacgaugcgg | AUAACGAUUCGGCAUUCACUAACUUCUCGU | cagacgacucgcccga | 30 |
| C3c 3 | gggaggacgaugcgg | AUGACGAUUCGGCAUUCACUAACUUCUCGU | cagacgacucgcccga | 31 |
| C3C 155 | gggaggacgaugcgg | AUGACGAUUCGGCAUUCACUAACUUCUCAU | cagacgacucgcccga | 32 |
| C3C 109 | gggaggacgaugcgg | AUGACGAUUCGGCAUUCACUAACUUCUACU | cagacgacucgcccga | 33 |
| C3-A 18c | gggaggacgaugcgg | AUCUGAGCCUAAAGUCAUUGUGAUCAUCCU | cagacgacucgcccga | 34 |

TABLE 3-continued

Human C3 2'F-RNA sequences*

| Clone No. | | | | SEQ ID NO: |
|---|---|---|---|---|
| C3c 35 | gggaggacgaugcggg | CGUUGGCGAUUCCUAAGUGUCGUUCUCGU | cagacgacucgcccga | 35 |
| C3B 41 | gggaggacgaugcggg | CGUCUCGAGCUCUAUGCGUCCUCUGUGGU | cagacgacucgcccga | 36 |
| C3B 108 | gggaggacgaugcgg | CGUCACGAGCUUUAUGCGUUCUCUGUGGU | cagacgacucgcccga | 37 |
| C3c 77 | gggaggacgaugcgg | CUUAAAGUUGUUUAUGAUCAUUCCGUACGU | cagacgacucgcccga | 38 |
| C3B 102 | gggaggacgaugcgg | GCGUUGGCGAUUGGUAAGUGUCGUUCUCGU | cagacgacucgcccga | 39 |
| c3a 9c | gggaggacgaugcgg | GCGUCUCGAGCUUUAUGCGUUCUCUGUGGU | cagacgacucgcccga | 40 |
| C3B 138 | gggaggacgaugcgg | GCGUCUCGAGCUCUAUGCGUUCUCUGUGGU | cagacgacucgcccga | 41 |
| c3-8c | ggaggacgaugcgg | GGCCUAAAGUCAAGUGAUCAUCCCCUGCGU | cagacganucgcccga | 42 |
| C3-23C | gggaggacgaugcgg | GUGGCGAUUCCAAGUCUUCCGUGAACAUGGU | cagacgacucgcccg | 43 |
| C3c 36 | gggaggacgaugcgg | GUGACUCGAUAUCUUCCAAUCUGUACAUGGU | cagacgacucncccga | 44 |
| 188 | gggaggacgaugcgg | UGGCGAUUCCAAGUCUUCCGUGAACAUGGU | cagacgacucgcccga | 45 |
| C3B 23 | gggaggacgaugcgg | UGGCGAUUCCAAGUCUUCCGUGAACAU | cagacgacucgcccga | 46 |

*Lower case letters represent the fixed region

TABLE 4

Human C5 2'F-RNA Sequences*

| Clone No: | | | | SEQ ID NO: |
|---|---|---|---|---|
| Group I | | | | |
| e5c/e11 | gggaggacgaugcgg | UCCGGCGCGCUGAGUGCCGGU UAUCCUCGU | cagacgacucgcccga | 47 |
| a6 | gggaggacgaugcgg | UCCGGCGCGCUGAGUGCCGGUUUAUCCUCGU | cagacgacucgcccga | 48 |
| f8 | gggaggacgaugcgg | UCUCAUGCGCCGAGUGUGAGUUUACCUUCGU | cagacgacucgcccga | 49 |
| K7 | gggaggacgaugcgg | UCUCAUGCGUCGAGUGUGAGUUUAACUGCGU | cagacgacucgcccga | 50 |
| c6 | gggaggacgaugcgg | UCUCAUGCGUCGAGUGUGAGUUUACCUUCGU | cagacgacucgcccga | 51 |
| g7 | gggaggacgaugcgg | UCUGCUACGCUGAGUGGCUGUUUACCUUCGU | cagacgacucgcccga | 52 |
| h1 | gggaggacgaugcgg | UCGGAUGCGCCGAGUCUCCGUUUUACCUUCGU | cagacgacucgcccga | 53 |
| Group II | | | | |
| f11 | gggaggacgaugcgg | UGAGCGCGUAUAGCGGUUUCGAUAGAGCUGCGU | cagacgacucgcccga | 54 |
| h2 | gggaggacgaugcgg | UGAGCGCGUAUAGCGGUUUCGAUAGAGCCU | cagacgacucgcccga | 55 |
| h6 | gggaggacgaugcgg | UGAGCGUGGCAAACGGUUUCGAUAGAGCCU | cagacgacucgcccga | 56 |
| h8 | gggaggacgaugcgg | UGAGCGUGUAAAACGGUUUCGAUAGAGCCU | cagacgacucgcccga | 57 |
| c9 | gggaggacgaugcgg | UGAGCGUGUAAAACGGUUUCGAUAGAGCCU | cagacgacucgcccga | 58 |
| c12 | gggaggacgaugcgg | UGGGCGUCAGCAUUUCGAUCUUCGGCACCU | cagacgacucgcccga | 59 |
| g9 | gggaggacgaugcgg | GAGUUGUUCGGCAUUUAGAUCUCCGCUCCCU | cagacgacucgcccga | 60 |
| f7 | gggaggacgaugcgg | GCAAAGUUCGGCAUUCAGAUCUCCAUGCCU | cagacgacucgcccga | 61 |
| E9c | gggaggacgaugcgg | GGCUUCUCACAUAUUCUUCUCUUUCCCCGU | cagacgacucgcccga | 62 |
| E4c | gggaggaggaucgg | UGUUCAGCAUUCAGAUCUU | cagacgacucgcccga | 63 |
| g3 | gggaggacgaugcgg | UGUUCAGCAUUCAGN/AUCUUCACGUGUCGU | cagacgacucgcccga | 64 |
| f6 | gggaggacgaugcgg | UGUUCACCAUUCAGAUCUUCACGUGUCGU | cagacgacucgcccga | 65 |
| d9 | gggaggacgaugc | UGUUCAGCAUUCAGAUCUUCACGUGUGU | cagacgacucgcccga | 66 |
| f4 | gggaggacgaugcgg | UUUCGAUAGAGACUUACAGUUGAGCGCGGU | cagacgacucgcccga | 67 |
| d3 | gggaggacgaugcgg | UUUGUGAUUUGGAAGUGGGGGGGAUAGGGU | cagacgacucgcccga | 68 |
| f9 | gggaggacgaugcgg | UGAGCGUGGCAAACGGUUUCGAUAGAGCCU | cagacgacucgcccga | 69 |
| J1c | ggagggcgauggGG | UGAGCGUGUAAAAGGUUUCGAUAGAGCCU | cagacgacucgcccga | 70 |
| d6 | gggaggacgaugcgg | GUAUCUUAUCUUGUUUUCGUUUUUCUGCCCU | cagacgaucgcccga | 71 |
| e8x | gggaggacgaugcgg | AGGGUUCUUUUCAUCUUCUUUCUUUCCCCU | cagacgacucgcccga | 72 |
| h11 | gggaggacgaugcgg | ACGAAGAAGGUGGUGGAGGAGUUUCGUGCU | cagacgacucgcccga | 73 |
| g10 | gggaggacgaugcgg | ACGAAGAAGGGGUGGAGGAGUUUCGUGCU | cagacgacucgcccga | 74 |

*Lower case letters represent the fixed region.

TABLE 5

Rat C5 2'F- RNA Sequences*

| Clone No: | | | | SEQ ID NO: |
|---|---|---|---|---|
| RtC5-116 | gggaggacgaugcgg | CGAUUACUGGGACGGACUCGCGAUGUGAGCC | cagacgacucgcccga | 76 |
| RtC5-39 | gggaggacgaugcgg | CGAUUACUGGGACAGACUCGCGAUGUGAGCU | cagacgacucgcccga | 77 |
| RtC5-69 | gggaggacgaugcgg | CGACUACUGGGAAGGG UCGCGAAGUGAGCC | cagacgacucgcccga | 78 |
| RtC5-95 | gggaggacgaugcgg | CGAUUACUGGGACAGACUCGCGAUGUGAGCU | cagacgacucgcccga | 79 |

TABLE 5-continued

Rat C5 2'F- RNA Sequences*

| Clone No: | | | SEQ ID NO: |
|---|---|---|---|
| RtC5-146 | gggaggacgaugcgg | CGACUACUGGGAGAGU ACGCGAUGUGUGCC | cagacgacucgcccga 80 |
| RtC5-168 | gggaggacgaugcgg | GUCCUCGGGGAAAAUUUCGCGACGUGAACCU | cagacgacucgcccga 81 |
| RtC5-74 | gggaggacgaugcgg | CUUCUGAAGAUUAUUUCGCGAUGUGAACUUCAGACCCCU | cagacgacucgcccga 82 |
| RtC5-100 | gggaggacgaugcgg | CUUCUGAAGAUUAUUUCGCGAUGUGAACUCCAGACCCCU | cagacgacucgcccga 83 |

*Lower case letters represent the fixed region.

TABLE 6

Human C1q 2'F-RNA Sequences*

| Clone NO: | | | SEQ ID NO: |
|---|---|---|---|
| c1qrd17-33c | gggaggacgaugcgg | AAAGUGGAAGUGAAUGGCCGACUUGUCUGGU | cagacgacucgcccga 84 |
| C1B100 | gggaggacgaugcgg | AAACCAAAUCGUCGAUCUUUCCACCG UCGU | cagacgacucgcccga 85 |
| c1q-a8c | gggaggacgaugcgg | AACACGAAACGGAGGUUGACUCGAUCUGGC | cagacgacucgcccga 86 |
| C1q5 c | ggaggacgaugcgg | AACACGGAAGACGUGCGACUCGAUCUGGU | cagacgacucgcccga 87 |
| 32.C1B76c | gggaggacgaugcgg | AACAAGGACAAAAGUGCGAUUCUGUCUGG | cagacgacucgccc 88 |
| c110c | gggaggacgaugcgg | AACAGACGACUCGCGCAACUACUCUGACGU | cagacgacucgcccga 89 |
| C1B121c | gggaggacgaugcgg | AACAGGUAGUUUGGGUGACUCUGUGUGACCU | cagacgacucgcccga 90 |
| C1q11c | ggaggacgaugcgg | AACCAAAUCGUCGAUCUUUCCACCGCUCGU | cagacgacucgcccga 91 |
| C15c | gggaggacgaugcgg | AACCGCUAUUGAAUGCACUGCUUCGUGCU | cagacgacucgcccga 92 |
| C1Q-A24'c | gggaggacgaugcgg | AACCGCAUGAGUUAGCCUGGCUCGCCUCGU | cagacgacucgcccga 93 |
| C1Q-A5'c | gggaggacgaugcgg | AACCCAAUCGUCUAAUCGCUGCUCAUCGU | cagacgacucgcccga 94 |
| C121c | gggaggacgaugcgg | AACUCAAUGGGCCUACUUUUCCGUGGUCCU | cagacgacucgcccga 95 |
| c1q-a2C | gggaggacgaugcgg | AAGCGGUGAGUCGUGGCUUUCUCCUCGAUCCUCGU | cagacgacucgcccga 96 |
| c1q-a12C | gggaggacgaugcgg | AAGGAUGACGAGGUGGUUGGGGUUUGUGCU | cagacgacucgcccga 97 |
| c1qrd17-43c | gggaggacgaugcgg | ACAAGACGAGAACGGGGGGAGCUACCUGGC | cagacgacucgcccga 98 |
| C1Q-A7'C | gggaggacgaugcgg | AGACACUAAACAAAUUGGCGACCUGACCGU | cagacgacucgcccga 99 |
| 03.C1Q.137c | gggaggacgaugcgg | AGAGGCUCAGACGACUCGACCACGGAUGCGACCU | cagacgacucgcccga 100 |
| 14.C1Q156c | gggaggacgaugcgg | AGAUGGAUGGAAGUGCUAGCUUCUGGGGU | cagacgacucgccc 101 |
| C1B119c | gggaggacgaugcgg | AGAUGGAUGGAAGUGCUAGUCUUUCUGGGGU | cagacgacucgcccga 102 |
| C1Q-A28'C | gggaggacgaugcgg | AGCAGUUGAAAGACGUGCGUUUCGUUUGU | cagacgacucgcccga 103 |
| 15.C1Q.157c | gggaggacgaugcgg | AGCACAAUUUUUCCUUUUCUUUUCGUCCACGUGCU | cagacgacucgcccga 104 |
| 44c1qb6oc | gggaggacgaugcgg | AGCUGAUGAAGAUGAUCUCUGACCCCU | cagacgacucgcccga 105 |
| 06.C1Q.143c | gggaggacgaugcgg | AGCUGAAAGCGAAGUGCGAGGUGUUUGGUC | cagacgacucgcccga 106 |
| C1q4c | ggaggacgaugcgg | AGCGAAAGUGCGAGUGAUUGACCAGGUGCU | cagacgacucgcccga 107 |
| c1qrd17-52c | gggaggacgaugcgg | AGCGUGAGAACAGUUGCGAGAUUGCCUGGU | cagacgacucgcccga 108 |
| C111c | gggaggacgaugcgg | AGGAGAGUGUGGUGAGGGUCGUUUUGAGGGU | cagacgacucgcccga 109 |
| 44c1Qb60c | gggaggacgaugcgg | AGGAGCUGAUGAAGAUGAUCUCUGACCCCU | cagacgacucgcccga 110 |
| 24c1qb51c | gggaggacgaugcgg | AGUUCCCAGCCGCCUUGAUUUCUCCGUGGU | cagacgacucgcccga 111 |
| 31c1qb16c | gggaggacgaugcgg | AUAAGUGCGAGUGUAUGAGGUGCGUGUGGU | cagacgacucgcccga 112 |
| 28c1Qb20c | gggaggacgaugcgg | AUCUGAGGAGCUCUUCGUCGUGCUGAGGGU | cagacgacucgcccga 113 |
| c1qrd17-61c | gggaggacgaugcgg | AUCCGAAUCUUCCUUACACGUCCUGCUCGU | cagacgacucgcccga 114 |
| C1q17c | ggaggacgaugcgg | AUCCGCAAACCGACUCGAGUUCCGU | cagacgacucgcccga 115 |
| 34c1qb27c | gggaggacgaugcgg | AUGGUACUUUAGUCUUCCUUGAUUCCGCCU | cagacgacucgcccga 116 |
| C1ql6c | gggaggacgaugcgg | AUGAUGACUGAACGUGCGACUCGACCUGGC | cagacgacucgcccga 117 |
| C1q7c | ggaggacgaugcgg | AUGAGGAGGAAGAGUCUGAGGUGCUGGGGU | cagacgacucgcccga 118 |
| C1Q-A22'C | gggaggacgaugcgg | AUUUCGGUCGACUAAAUAGGGGUGGCUCGU | cagacgacucgcccga 119 |
| C122c | gggaggacgaugcgg | CAAGAGGUCAGACGACUGCCCCGAGUCCUCCCCCGGU | cagacgacucgcccga 120 |
| C115c | gggaggacgaugcgg | CAGUGAAAGGCGAGUUUUCUCCCUCUCCCU | cagacgacucgcccga 121 |
| 09.C1Q.149c | gggaggacgaugcgg | CAUCGUUCAGGAGAACUACACUUCGCUCUU | cagacgacucgcccga 122 |
| 04.C1Q.138c | gggaggacgaugcgg | CAUCUUCCUUGUUCUUCCAACCGUGCUCCU | cagacgacucgcccga 123 |
| C1Q-A4'C | gggaggacgaugcgg | CAUCGUAAACAAUUUGUUCCAUCUCCGCCU | cagacgacucgcccga 124 |
| c1qrd17-64c | gggaggacgaugcgg | CAUUGUCCAAGUUUAGCUGUCCGUGCUCGU | cagacgacucgcccga 125 |
| 46C1Qb64c | gggaggacgaugcgg | CAUAGUCCGGAUACUAGUCACCAGCCUCGU | agacgacucgcccga 126 |
| C1q6 c | gggaggacgaugcgg | CCGUCUCGAUCCUUCUAUGCCUUCGCUCGU | cagacgacucgcccga 127 |
| 23C1Qb4x | gggaggacgaugcgg | CGGGAAGUUUGAGGUGUANUACCUGUUGUCUGGU | cagacgacucgcccga 128 |
| c1qrd17-63c | gggaggacgaugcgg | CUCAACUCUCCCACAGACGACUCGCCCGGGCUCCU | cagacgacucgcccga 129 |
| c1qrd17-47c | gggaggacgaugcgg | GACUCCUCGACCGACUCGACCGGCUCGU | cagacgacucgccga 130 |
| C1q9c | ggaggacgaugcgg | GAACCAAAUCGUCGAUCUUUCCACCGCUCGU | cagacgacucgcccga 131 |
| C1Q-A10'C | gggaggacgaugcgg | GACCACCUCGAUCCUCAGCGCCAUUGCCCU | cagacgacucgcccga 132 |
| C119c | gggaggacgaugcgg | GAAGUGGAAGGGUAGUUGUGUGACCU | cagacgacucgcccga 133 |

TABLE 6-continued

Human C1q 2'F-RNA Sequences*

| Clone NO: | | | | SEQ ID NO: |
|---|---|---|---|---|
| c1qrd17-42c | cggaggacgaugcgg | GCAAACUUUUCCUUUUCCCUUUAUCUUCCUUGCCCU | cagacgacucgcccga | 134 |
| 30c1Q24c | gggaggacgaugcgg | GGCCGACGAUUCACCAAUGUUCUCUCUGGU | cagacgacucgcccga | 135 |
| C1q10c | ggaggacgaugcgg | GGUUCCUCAAUGACGAUCUCCAUUCCGCUCGU | cagacgacucgcccag | 136 |
| C1q20c | ggaggacgaugcgg | GUCGACAUUGAAGCUGCUCUGCCUUGAUCCU | cagacgacucgcccga | 137 |
| 08.C1Q.147c | gggaggacgaugcgg | UCCAAUUCGUUCUCAUGCCUUUCCGCUCGU | cagacgacucgcccga | 138 |
| 11.C1Q.152c | gggaggacgaugcgg | UCCGCAAGUUUAGCACUCACUGCCUCGU | cagacgacucgcccga | 139 |
| 26c1Qb4c | gggaggacgaugcgg | UCCACAUCGAAUUUUCUGUCCGUUCGU | cagacgacucgcccga | 140 |
| C1B115c | gggaggacgaugcgg | UCGAUGUUCUUCCUCACCACUGCUCGUCGCCU | cagacgacucgcccga | 141 |
| 33c1Q26c | gggaggacgaugcgg | UCGAGCUGAGAGGGGCUACUUGUUCUGGUCA | cagacgacucgcccga | 142 |
| 01.C1Q.135c | gggaggacgaugcgg | UGGAAGCGAAUGGGCUAGGGUGGGCUGACCUC | cagacgacucgcccga | 143 |
| 47c1qb65c | gggaggacgaugcgg | UGGACUUCUUUUCCUCUUCCUCCUUCCGCCGGU | cagacgacucgcccga | 144 |
| C1q14c | ggaggacgaugcgg | UUCCAAAUCGUCUAAGCAUCGCUCGCUCGU | cagacgacucgcccag | 145 |
| c1qrd17-53c | gggaggacgaugcgg | UUCCACAUCGCAAUUUUCUGUCCGUGCUCGU | cagacgacucgcccga | 146 |
| c1q-a6C | gggaggacgaugcgg | UUCCACAUCGAAUUUUCUGUCCGUGUCGU | cagacgacucgcccga | 147 |
| C1B114c | gggaggacgaugcgg | UUCCGAUCGACUCCACAUACAUCUGCUCGU | cagacgacucgcccga | 148 |
| c1qrd17-56c | gggaggacgaugcgg | UUCCGACAUCGAUGUUGCUCUUCGCCUCGU | cagacgacucgcccga | 149 |
| 05.C1Q.142c | gggaggacgaugcgg | UUCCGAAGUUCUUCCCCCGAGCCUUCCCCCUC | cagacgacucgcccga | 150 |
| 30c1q24c | gggaggacgaugcgg | UUCCGACGAUUCUCCAAUGUUCUCUCUGGU | cagacgacucgcccga | 151 |
| 38c1qb45c | gggaggacgaugcgg | UUCCGACGAUUCUCCAAUCUUCUCUCUGGU | cagacgacucgcccga | 152 |
| 10.C1Q151c | gggaggacgaugcgg | UUCCGCAAGUUUAGACACUCACUGCCUCGU | cagacgacucgcccga | 153 |
| C113x | gggaggacgaugcgg | UUCCGCAAAGUAGAUAUNUCAUCCGCACGU | cagacgacucgcccga | 154 |
| 10.C1B.134c | gggaggacgaugcgg | UUGAGUGGACAGUGCGAUUCGUUUUGGGGU | cagacgacucgcccga | 155 |

*Lower case letters represent the fixed region.

We claim:

1. A purified and non-naturally occurring RNA Ligand to C1q, wherein said ligand is selected from the group consisting of SEQ ID NOS:84–155.

2. A purified and non-naturally occurring RNA Ligand to C3, wherein said ligand is selected from the group consisting of SEQ ID NOS:21–46.

3. A purified and non naturally occurring RNA Ligand to C5, wherein said ligand is selected from the group consisting of SEQ ID NOS:47–83.

* * * * *

SEQUENCE LISTING (1) GENERAL INFORMATION:

(iii) NUMBER OF SEQUENCES: 157

(2) INFORMATION FOR SEQ ID NO: 1:

(i) SEQUENCE CHARACTERISTICS:
      (A) LENGTH: 98 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

TAATACGACT CACTATAGGG AGGACGATGC GGNNNNNNNN NNNNNNNNNN     50

NNNNNNNNNN NNNNNNNNNN NNNNNNNNNN NNCAGACGAC TCGCCCGA     98

(2) INFORMATION FOR SEQ ID NO: 2:

(i) SEQUENCE CHARACTERISTICS:
      (A) LENGTH: 81 base pairs
      (B) TYPE: nucleic acid
      (C) STRANDEDNESS: single
      (D) TOPOLOGY: linear (ii) MOLECULE TYPE: RNA (xi) SEQUENCE DESCRIPTION: SEQ ID NO: 2:

GGGAGGACGA UGCGGNNNNN NNNNNNNNNN NNNNNNNNNN NNNNNNNNNN     50

NNNNNNNNNN NNNNNCAGAC GACUCGCCCG A     81

(2) INFORMATION FOR SEQ ID NO: 3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

TAATACGACT CACTATAGGG AGGACGATGC GG                      32

(2) INFORMATION FOR SEQ ID NO: 4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

TCGGGCGAGT CGTCTG                                               16

(2) INFORMATION FOR SEQ ID NO: 5:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 5:

GGGAGGACGA UGCGGGAGGA GUGGAGGUAA ACAAUAGGUC GGUAGCGACU          50

CCCACUAACA GGCCUCAGAC GACUCGCCCG A                               81

(2) INFORMATION FOR SEQ ID NO: 6:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'-NH2 modified (xi) SEQUENCE DESCRIPTION: SEQ ID NO: 6:

GGGAGGACGA UGCGGGUGGA GUGGAGGUAA ACAAUAGGUC GGUAGCGACU          50

CCCAGUAACG GCCUCAGACG ACUCGCCCGA                                80

(2) INFORMATION FOR SEQ ID NO: 7:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: RNA (ix) FEATURE:
            (D) OTHER INFORMATION:  All pyrimidines are 2'-NH2 modified (xi) SEQUENCE DESCRIPTION: SEQ ID NO: 7:

GGGAGGACGA UGCAAGUGGA GUGGAGGUAU AACGGCCGGU AGGCAUCCCA           50

CUCGGGCCUA GCUCAGACGA CUCGCCCGA                                 79

(2) INFORMATION FOR SEQ ID NO: 8:

(i) SEQUENCE CHARACTERISTICS:
            (A) LENGTH: 79 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-NH2 modified (xi) SEQUENCE DESCRIPTION: SEQ ID NO: 8:

GGGAGGACGA UGCGGGUGGA GUGGGGAUCA UACGGCUGGU AGCACGAGCU           50

CCCUAACAGC GGUCAGACGA CUCGCCCGA                                 79

(2) INFORMATION FOR SEQ ID NO: 9:

(i) SEQUENCE CHARACTERISTICS:
            (A) LENGTH: 80 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-NH2 modified (xi) SEQUENCE DESCRIPTION: SEQ ID NO: 9:

GGGAGGACGA UGCGGGAGGA GUGGAGGUAA ACAAUAGGCC GGUAGCGACU           50

CCCACUAACA GCCUCAGACG ACUCGCCCGA                                80

(2) INFORMATION FOR SEQ ID NO: 10:

(i) SEQUENCE CHARACTERISTICS:
            (A) LENGTH: 80 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  All pyrimidines are 2'-NH2 modified (xi) SEQUENCE DESCRIPTION: SEQ ID NO: 10:

GGGAGGACGA UGCGGUGGAG UGGAGGUAUA CCGGCCGGUA GCGCAUCCCA           50

CUCGGGUCUG UGCUCAGACG ACUCGCCCGA                                80

(2) INFORMATION FOR SEQ ID NO: 11:

(i) SEQUENCE CHARACTERISTICS:
            (A) LENGTH: 80 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION: All pyrimidines are 2'-NH2 modified (xi) SEQUENCE DESCRIPTION: SEQ ID NO: 11:

GGGAGGACGA UGCGGGUGGA GCGGAGGUUU AUACGGCUGG UAGCUCGAGC           50

UCCCUAACAC GCGGUAGACG ACUCGCCCGA                                80

(2) INFORMATION FOR SEQ ID NO: 12:

(i) SEQUENCE CHARACTERISTICS:
           (A) LENGTH: 80 base pairs
           (B) TYPE: nucleic acid
           (C) STRANDEDNESS: single
           (D) TOPOLOGY: linear (ii) MOLECULE TYPE: RNA (ix) FEATURE:
            (D) OTHER INFORMATION: All pyrimidines are 2'-NH2 modified (xi) SEQUENCE DESCRIPTION: SEQ ID NO: 12:

GGGAGGACGA UGCGGGUGGA GUGGAGGUAU AACGGCCGGU AGCGCAUCCC           50

ACUCGGGUCU GCGGUAGACG ACUCGCCCGA                                80

(2) INFORMATION FOR SEQ ID NO: 13:

(i) SEQUENCE CHARACTERISTICS:
           (A) LENGTH: 80 base pairs
           (B) TYPE: nucleic acid
           (C) STRANDEDNESS: single
           (D) TOPOLOGY: linear (ii) MOLECULE TYPE: RNA (ix) FEATURE:
            (D) OTHER INFORMATION: All pyrimidines are 2'-NH2 modified (xi) SEQUENCE DESCRIPTION: SEQ ID NO: 13:

GGGAGGACGA UGCGGGUGGA GUGGAGGGUA AACAAUGGCU GGUGGCAUUC           50

GGAAUCUCCC GCGGUAGACG ACUCGCCCGA                                80

(2) INFORMATION FOR SEQ ID NO: 14:

(i) SEQUENCE CHARACTERISTICS:
           (A) LENGTH: 79 base pairs
           (B) TYPE: nucleic acid
           (C) STRANDEDNESS: single
           (D) TOPOLOGY: linear (ii) MOLECULE TYPE: RNA (ix) FEATURE:
            (D) OTHER INFORMATION: All pyrimidines are 2'-NH2 modified (xi) SEQUENCE DESCRIPTION: SEQ ID NO: 14:

GGGAGGACGA UGCGGGUUGC UGGUAGCCUG AUGUGGGUGG AGUGAGUGGA           50

GGGUUGAAAA AUGCAGACGA CUCGCCCGA                                 79

(2) INFORMATION FOR SEQ ID NO: 15:

(i) SEQUENCE CHARACTERISTICS:
           (A) LENGTH: 79 base pairs
           (B) TYPE: nucleic acid
           (C) STRANDEDNESS: single

```
      (D) TOPOLOGY: linear (ii) MOLECULE TYPE: RNA (ix) FEATURE:
        (D) OTHER INFORMATION:  All pyrimidines are 2'-NH2 modified (xi) SEQUENCE DESCRIPTION: SEQ ID NO: 15:

GGGAGGACGA UGCGGCUGGU AGCAUGUGCA UUGAUGGGAG GAGUGGAGGU            50

CACCGUCAAC CGUCAGACGA CUCGCCCGA                                  79

(2) INFORMATION FOR SEQ ID NO: 16:

(i) SEQUENCE CHARACTERISTICS:
       (A) LENGTH: 81 base pairs
       (B) TYPE: nucleic acid
       (C) STRANDEDNESS: single
       (D) TOPOLOGY: linear (ii) MOLECULE TYPE: RNA (ix) FEATURE:
        (D) OTHER INFORMATION:  All pyrimidines are 2'-NH2 modified (xi) SEQUENCE DESCRIPTION: SEQ ID NO: 16:

GGGAGGACGA UGCGGUUUCU CGGCCAGUAG UUUGCGGGUG GAGUGGAGGU            50

AUAUCUGCGU CCUCGCAGAC GACUCGCCCG A                               81

(2) INFORMATION FOR SEQ ID NO: 17:

(i) SEQUENCE CHARACTERISTICS:
       (A) LENGTH: 81 base pairs
       (B) TYPE: nucleic acid
       (C) STRANDEDNESS: single
       (D) TOPOLOGY: linear (ii) MOLECULE TYPE: RNA (ix) FEATURE:
        (D) OTHER INFORMATION:  All pyrimidines are 2'-NH2 modified (xi) SEQUENCE DESCRIPTION: SEQ ID NO: 17:

GGGAGGACGA UGCGGCACCU CACCUCCAUA UUGCCGGUUA UCGCGUAGGG            50

UGAGCCCAGA CACGACAGAC GACUCGCCCG A                               81

(2) INFORMATION FOR SEQ ID NO: 18:

(i) SEQUENCE CHARACTERISTICS:
       (A) LENGTH: 80 base pairs
       (B) TYPE: nucleic acid
       (C) STRANDEDNESS: single
       (D) TOPOLOGY: linear (ii) MOLECULE TYPE: RNA (ix) FEATURE:
        (D) OTHER INFORMATION:  All pyrimidines are 2'-NH2 modified (xi) SEQUENCE DESCRIPTION: SEQ ID NO: 18:

GGGAGGACGA UGCGGCACUC ACCUUCAUAU UGGCCGCCAU CCCCAGGGUU            50

GAGCCCAGAC ACAGCAGACG ACUCGCCCGA                                 80

(2) INFORMATION FOR SEQ ID NO: 19:

(i) SEQUENCE CHARACTERISTICS:
       (A) LENGTH: 81 base pairs
       (B) TYPE: nucleic acid
```

(C) STRANDEDNESS: single
(D) TOPOLOGY: linear (ii) MOLECULE TYPE: RNA (ix) FEATURE:
(D) OTHER INFORMATION: All pyrimidines are 2'-NH2 modified (xi) SEQUENCE DESCRIPTION: SEQ ID NO: 19:

GGGAGGACGA UGCGGGCAUA GUGGGCAUCC CAGGGUUGCC UAACGGCAUC           50

CGGGGUUGUU AUUGGCAGAC GACUCGCCCG A                              81

(2) INFORMATION FOR SEQ ID NO: 20:

(i) SEQUENCE CHARACTERISTICS:
(A) LENGTH: 79 base pairs
(B) TYPE: nucleic acid
(C) STRANDEDNESS: single
(D) TOPOLOGY: linear (ii) MOLECULE TYPE:RNA (ix) FEATURE:
(D) OTHER INFORMATION: All pyrimidines are 2'-NH2 modified (xi) SEQUENCE DESCRIPTION: SEQ ID NO: 20:

GGGAGGACGA UGCGGCAGAC GACUCGCCCG AGGGGAUCCC CCGGGCCUGC           50

AGGAAUUCGA UAUCAGACGA CUCGCCCGA                                 79

(2) INFORMATION FOR SEQ ID NO:21:

(i) SEQUENCE CHARACTERISTICS:
(A) LENGTH: 62 base pairs
(B) TYPE: nucleic acid
(C) STRANDEDNESS: single
(D) TOPOLOGY: linear (ii) MOLECULE TYPE:RNA (ix) FEATURE:
(D) OTHER INFORMATION: All pyrimidines are 2'-F modified (xi) SEQUENCE DESCRIPTION: SEQ ID NO:21:

GGGAGGACGA UGCGGAACUC AAUGGGCCUA CUUUUUCCGU GGUCCUCAGA           50

CGACUCGCCC GA                                                   62

(2) INFORMATION FOR SEQ ID NO:22:

(i) SEQUENCE CHARACTERISTICS:
(A) LENGTH: 61 base pairs
(B) TYPE: nucleic acid
(C) STRANDEDNESS: single
(D) TOPOLOGY: linear (ii) MOLECULE TYPE:RNA (ix) FEATURE:
(D) OTHER INFORMATION: All pyrimidines are 2'-F modified (xi) SEQUENCE DESCRIPTION: SEQ ID NO:22:

GGGAGGACGA UGCGGAACUC AAUGGGCCUA CUUUUCCGUG GUCCUCAGAC           50

GACUCGCCCG A                                                    61

(2) INFORMATION FOR SEQ ID NO:23:

(i) SEQUENCE CHARACTERISTICS:
(A) LENGTH: 60 base pairs (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:23:

GGGAGGACGA UGCGGAACUC AAUGGGCCGA CUUUUUCCGU GUCCUCAGAC          50

GACUCGCCCG                                                      60

(2) INFORMATION FOR SEQ ID NO:24:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:24:

GGGAGGACGA UGCGGAACUC AAUGGGCCGA CUUUCCGUGG UCCUCAGACG          50

ACUCGCCCGA                                                      60

(2) INFORMATION FOR SEQ ID NO:25:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:25:

GGGAGGACGA UGCGGAACUC AAUGGGCNUA CUUUUCCGUG GUCCUCAGAC          50

GACUCGCCCG A                                                    61

(2) INFORMATION FOR SEQ ID NO:26:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:26:

GGGAGGACGA UGCGGAACUC AAUGGGCCGA CUUUUCCGUG GUCCUCAGAC          50

GACUCGCCCG A                                                    61

(2) INFORMATION FOR SEQ ID NO:27:

(i) SEQUENCE CHARACTERISTICS:

(A) LENGTH: 60 base pairs
       (B) TYPE: nucleic acid
       (C) STRANDEDNESS: single
       (D) TOPOLOGY: linear (ii) MOLECULE TYPE:RNA (ix) FEATURE:
       (D) OTHER INFORMATION: All pyrimidines are 2'-F modified (xi) SEQUENCE DESCRIPTION: SEQ ID NO:27:

GGGAGGACGA UGCGGAACUC AAUGGGCCGA CUUUUCCGUG GUCCUCAGAC            50

GACUGCCCGA                                                       60

(2) INFORMATION FOR SEQ ID NO:28:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (ii) MOLECULE TYPE:RNA (ix) FEATURE:
       (D) OTHER INFORMATION: All pyrimidines are 2'-F modified (xi) SEQUENCE DESCRIPTION: SEQ ID NO:28:

GGGAGGACGA UGCGGACGCA GGGGAUGCUC ACUUUGACUU UAGGCCAGAC            50

GACUCGCCCG                                                       60

(2) INFORMATION FOR SEQ ID NO:29:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (ii) MOLECULE TYPE:RNA (ix) FEATURE:
       (D) OTHER INFORMATION: All pyrimidines are 2'-F modified (xi) SEQUENCE DESCRIPTION: SEQ ID NO:29:

GGGAGGACGA UGCGGACUCG GCAUUCACUA ACUUUUGCGC UCGUCAGACG            50

ACUCGCCCGA                                                       60

(2) INFORMATION FOR SEQ ID NO:30:

(i) SEQUENCE CHARACTERISTICS:
       (A) LENGTH: 61 base pairs
       (B) TYPE: nucleic acid
       (C) STRANDEDNESS: single
       (D) TOPOLOGY: linear (ii) MOLECULE TYPE:RNA (ix) FEATURE:
       (D) OTHER INFORMATION: All pyrimidines are 2'-F modified (xi) SEQUENCE DESCRIPTION: SEQ ID NO:30:

GGGAGGACGA UGCGGAUAAC GAUUCGGCAU UCACUAACUU CUCGUCAGAC            50

GACUCGCCCG A                                                     61

(2) INFORMATION FOR SEQ ID NO:31:

(i) SEQUENCE CHARACTERISTICS:
    (A) LENGTH: 61 base pairs
    (B) TYPE: nucleic acid
    (C) STRANDEDNESS: single
    (D) TOPOLOGY: linear (ii) MOLECULE TYPE:RNA (ix) FEATURE:
    (D) OTHER INFORMATION: All pyrimidines are 2'-F modified (xi) SEQUENCE DESCRIPTION: SEQ ID NO:31:

GGGAGGACGA UGCGGAUGAC GAUUCGGCAU UCACUAACUU CUCGUCAGAC       50

GACUCGCCCG A                                                 61

(2) INFORMATION FOR SEQ ID NO:32:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:32:

GGGAGGACGA UGCGGAUGAC GAUUCGGCAU UCACUAACUU CUCAUCAGAC       50

GACUCGCCCG A                                                 61

(2) INFORMATION FOR SEQ ID NO:33:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:33:

GGGAGGACGA UGCGGAUGAC GAUUCGGCAU UCACUAACUU CUACUCAGAC       50

GACUCGCCCG A                                                 61

(2) INFORMATION FOR SEQ ID NO:34:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:34:

GGGAGGACGA UGCGGAUCUG AGCCUAAAGU CAUUGUGAUC AUCCUCAGAC       50

GACUCGCCCG A                                                 61

(2) INFORMATION FOR SEQ ID NO:35:

```
    (i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:35:

GGGAGGACGA UGCGGGCGUU GGCGAUUCCU AAGUGUCGUU CUCGUCAGAC           50

GACUCGCCCG A                                                    61

(2) INFORMATION FOR SEQ ID NO:36:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:36:

GGGAGGACGA UGCGGCGUCU CGAGCUCUAU GCGUCCUCUG UGGUCAGACG           50

ACUCGCCCGA                                                      60

(2) INFORMATION FOR SEQ ID NO:37:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:37:

GGGAGGACGA UGCGGCGUCA CGAGCUUUAU GCGUUCUCUG UGGUCAGACG           50

ACUCGCCCGA                                                      60

(2) INFORMATION FOR SEQ ID NO:38:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:38:

GGGAGGACGA UGCGGCUUAA AGUUGUUUAU GAUCAUUCCG UACGUCAGAC           50

GACUCGCCCG A                                                    61
```

(2) INFORMATION FOR SEQ ID NO:39:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:39:

```
GGGAGGACGA UGCGGGCGUU GGCGAUUGGU AAGUGUCGUU CUCGUCAGAC        50

GACUCGCCCG A                                                  61
```

(2) INFORMATION FOR SEQ ID NO:40:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:40:

```
GGGAGGACGA UGCGGGCGUC UCGAGCUUUA UGCGUUCUCU GUGGUCAGAC        50

GACUCGCCCG A                                                  61
```

(2) INFORMATION FOR SEQ ID NO:41:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:41:

```
GGGAGGACGA UGCGGGCGUC UCGAGCUCUA UGCGUUCUCU GUGGUCAGAC        50

GACUCGCCCG A                                                  61
```

(2) INFORMATION FOR SEQ ID NO:42:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:42:

```
GGAGGACGAU GCGGGGCCUA AAGUCAAGUG AUCAUCCCCU GCGUCAGACG        50

ANUCGCCCGA                                                    60
```

(2) INFORMATION FOR SEQ ID NO:43:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:43:

```
GGGAGGACGA UGCGGGUGGC GAUUCCAAGU CUUCCGUGAA CAUGGUCAGA        50

CGACUCGCCC G                                                 61
```

(2) INFORMATION FOR SEQ ID NO:44:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:44:

```
GGGAGGACGA UGCGGGUGAC UCGAUAUCUU CCAAUCUGUA CAUGGUCAGA        50

CGACUCNCCC GA                                                62
```

(2) INFORMATION FOR SEQ ID NO:45:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:45:

```
GGGAGGACGA UGCGGUGGCG AUUCCAAGUC UUCCGUGAAC AUGGUCAGAC        50

GACUCGCCCG A                                                 61
```

(2) INFORMATION FOR SEQ ID NO:46:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:46:

```
GGGAGGACGA UGCGGUGGCG AUUCCAAGUC UUCCGUGAAC AUCAGACGAC        50

UCGCCCGA                                                     58
```

(2) INFORMATION FOR SEQ ID NO:47:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:47:

```
GGGAGGACGA UGCGGUCCGG CGCGCUGAGU GCCGGUUAUC CUCGUCAGAC        50

GACUCGCCCG A                                                  61
```

(2) INFORMATION FOR SEQ ID NO:48:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:48:

```
GGGAGGACGA UGCGGUCCGG CGCGCUGAGU GCCGGUUUAU CCUCGUCAGA        50

CGACUCGCCC GA                                                 62
```

(2) INFORMATION FOR SEQ ID NO:49:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:49:

```
GGGAGGACGA UGCGGUCUCA UGCGCCGAGU GUGAGUUUAC CUUCGUCAGA        50

CGACUCGCCC GA                                                 62
```

(2) INFORMATION FOR SEQ ID NO:50:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:50:

```
GGGAGGACGA UGCGGUCUCA UGCGUCGAGU GUGAGUUUAA CUGCGUCAGA        50
```

```
CGACUCGCCC GA                                                                              62

(2) INFORMATION FOR SEQ ID NO:51:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:51:

GGGAGGACGA UGCGGUCUCA UGCGUCGAGU GUGAGUUUAC CUUCGUCAGA                                       50

CGACUCGCCC GA                                                                              62

(2) INFORMATION FOR SEQ ID NO:52:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:52:

GGGAGGACGA UGCGGUCUGC UACGCUGAGU GGCUGUUUAC CUUCGUCAGA                                       50

CGACUCGCCC GA                                                                              62

(2) INFORMATION FOR SEQ ID NO:53:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:53:

GGGAGGACGA UGCGGUCGGA UGCGCCGAGU CUCCGUUUAC CUUCGUCAGA                                       50

CGACUCGCCC GA                                                                              62

(2) INFORMATION FOR SEQ ID NO:54:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:54:

GGGAGGACGA UGCGGUGAGC GCGUAUAGCG GUUUCGAUAG AGCUGCGUCA                                       50
```

GACGACUCGC CCGA                                                64

(2) INFORMATION FOR SEQ ID NO:55:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:55:

GGGAGGACGA UGCGGUGAGC GCGUAUAGCG GUUUCGAUAG AGCCUCAGAC          50

GACUCGCCCG A                                                   61

(2) INFORMATION FOR SEQ ID NO:56:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:56:

GGGAGGACGA UGCGGUGAGC GUGGCAAACG GUUUCGAUAG AGCCUCAGAC          50

GACUCGCCCG A                                                   61

(2) INFORMATION FOR SEQ ID NO:57:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:57:

GGGAGGACGA UGCGGUGAGC GUGUAAAACG GUUUCGAUAG AGCCUCAGAC          50

GACUCGCCCG A                                                   61

(2) INFORMATION FOR SEQ ID NO:58:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:58:

GGGAGGACGA UGCGGUGAGC GUGUAAAACG GUUUCGAUAG AGCCUCAGAC           50

GACUCGCCCG A                                                   61

(2) INFORMATION FOR SEQ ID NO:59:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:59:

GGGAGGACGA UGCGGUGGGC GUCAGCAUUU CGAUCUUCGG CACCUCAGAC           50

GACUCGCCCG A                                                   61

(2) INFORMATION FOR SEQ ID NO:60:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:60:

GGGAGGACGA UGCGGGAGUU GUUCGGCAUU UAGAUCUCCG CUCCCUCAGA           50

CGACUCGCCC GA                                                  62

(2) INFORMATION FOR SEQ ID NO:61:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:61:

GGGAGGACGA UGCGGGCAAA GUUCGGCAUU CAGAUCUCCA UGCCCUCAGA           50

CGACUCGCCC GA                                                  62

(2) INFORMATION FOR SEQ ID NO:62:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:62:

```
GGGAGGACGA UGCGGGGCUU CUCACAUAUU CUUCUCUUUC CCCGUCAGAC         50

GACUCGCCCG A                                                  61

(2) INFORMATION FOR SEQ ID NO:63:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:63:

GGGAGGAGGA UCGGUGUUCA GCAUUCAGAU CUUCAGACGA CUCGCCCGA          49

(2) INFORMATION FOR SEQ ID NO:64:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:64:

GGGAGGACGA UGCGGUGUUC AGCAUUCAGN AUCUUCACGU GUCGUCAGAC         50

GACUCGCCCG A                                                  61

(2) INFORMATION FOR SEQ ID NO:65:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:65:

GGGAGGACGA UGCGGUGUUC ACCAUUCAGA UCUUCACGUG UCGUCAGACG         50

ACUCGCCCGA                                                    60

(2) INFORMATION FOR SEQ ID NO:66:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:66:
```

```
GGGAGGACGA UGCUGUUCAG CAUUCAGAUC UUCACGUGUG UCAGACGACU        50

CGCCCGA                                                      57
```

(2) INFORMATION FOR SEQ ID NO:67:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:67:

```
GGGAGGACGA UGCGGUUUCG AUAGAGACUU ACAGUUGAGC GCGGUCAGAC        50

GACUCGCCCG A                                                 61
```

(2) INFORMATION FOR SEQ ID NO:68:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:68:

```
GGGAGGACGA UGCGGUUUGU GAUUUGGAAG UGGGGGGGAU AGGGUCAGAC        50

GACUCGCCCG A                                                 61
```

(2) INFORMATION FOR SEQ ID NO:69:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:69:

```
GGGAGGACGA UGCGGUGAGC GUGGCAAACG GUUUCGAUAG AGCCUCAGAC        50

GACUCGCCCG A                                                 61
```

(2) INFORMATION FOR SEQ ID NO:70:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:70:

```
GGAGGGCGAU GGGGUGAGCG UGUAAAAGGU UGCGAUAGAG CCUCAGACGA          50

CUCGCCCGA                                                       59

(2) INFORMATION FOR SEQ ID NO:71:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:71:

GGGAGGACGA UGCGGGUAUC UUAUCUUGUU UUCGUUUUUC UGCCCUCAGA          50

CGAUCGCCCG A                                                    61

(2) INFORMATION FOR SEQ ID NO:72:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:72:

GGGAGGACGA UGCGGAGGGU UCUUUUCAUC UUCUUUCUUU CCCCUCAGAC          50

GACUCGCCCG A                                                    61

(2) INFORMATION FOR SEQ ID NO:73:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:73:

GGGAGGACGA UGCGGACGAA GAAGGUGGUG GAGGAGUUUC GUGCUCAGAC          50

GACUCGCCCG A                                                    61

(2) INFORMATION FOR SEQ ID NO:74:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified
```

(xi) SEQUENCE DESCRIPTION: SEQ ID NO:74:

GGGAGGACGA UGCGGACGAA GAAGGGGUG GAGGAGUUUC GUGCUCAGAC                50

GACUCGCCCG A                                                        61

(2) INFORMATION FOR SEQ ID NO:75:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:75:

GACGAUGCGG UCUCAUGCGU CGAGUGUGAG UUUACCUUCG UC                       42

(2) INFORMATION FOR SEQ ID NO:76:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:76:

GGGAGGACGA UGCGGCGAUU ACUGGGACGG ACUCGCGAUG UGAGCCCAGA               50

CGACUCGCCC GA                                                       62

(2) INFORMATION FOR SEQ ID NO:77:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:77:

GGGAGGACGA UGCGGCGAUU ACUGGGACAG ACUCGCGAUG UGAGCUCAGA               50

CGACUCGCCC GA                                                       62

(2) INFORMATION FOR SEQ ID NO:78:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:78:

```
GGGAGGACGA UGCGGCGACU ACUGGGAAGG GUCGCGAAGU GAGCCCAGAC        50

GACUCGCCCG A                                                  61

(2) INFORMATION FOR SEQ ID NO:79:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:79:

GGGAGGACGA UGCGGCGAUU ACUGGGACAG ACUCGCGAUG UGAGCUCAGA        50

CGACUCGCCC GA                                                 62

(2) INFORMATION FOR SEQ ID NO:80:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:80:

GGGAGGACGA UGCGGCGACU ACUGGGAGAG UACGCGAUGU GUGCCCAGAC        50

GACUCGCCCG A                                                  61

(2) INFORMATION FOR SEQ ID NO:81:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:81:

GGGAGGACGA UGCGGGUCCU CGGGGAAAAU UUCGCGACGU GAACCUCAGA        50

CGACUCGCCC GA                                                 62

(2) INFORMATION FOR SEQ ID NO:82:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified
```

(xi) SEQUENCE DESCRIPTION: SEQ ID NO:82:

GGGAGGACGA UGCGGCUUCU GAAGAUUAUU UCGCGAUGUG AACUUCAGAC    50

CCCUCAGACG ACUCGCCCGA    70

(2) INFORMATION FOR SEQ ID NO:83:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:83:

GGGAGGACGA UGCGGCUUCU GAAGAUUAUU UCGCGAUGUG AACUCCAGAC    50

CCCUCAGACG ACUCGCCCGA    70

(2) INFORMATION FOR SEQ ID NO:84:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:84:

GGGAGGACGA UGCGGAAAGU GGAAGUGAAU GGCCGACUUG UCUGGUCAGA    50

CGACUCGCCC GA    62

(2) INFORMATION FOR SEQ ID NO:85:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:85:

GGGAGGACGA UGCGGAAACC AAAUCGUCGA UCUUUCCACC GUCGUCAGAC    50

GACUCGCCCG A    61

(2) INFORMATION FOR SEQ ID NO:86:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:86:

GGGAGGACGA UGCGGAACAC GAAACGGAGG UUGACUCGAU CUGGCCAGAC        50

GACUCGCCCG A                                                  61

(2) INFORMATION FOR SEQ ID NO:87:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:87:

GGAGGACGAU GCGGAACACG GAAGACAGUG CGACUCGAUC UGGUCAGACG         50

ACUCGCCCGA                                                    60

(2) INFORMATION FOR SEQ ID NO:88:

(i) SEQUENCE CHARACTERISTICS:
            (A) LENGTH: 59 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:88:

GGGAGGACGA UGCGGAACAA GGACAAAAGU GCGAUUCUGU CUGGCAGACG         50

ACUCGCCCG                                                     59

(2) INFORMATION FOR SEQ ID NO:89:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:89:

GGGAGGACGA UGCGGAACAG ACGACUCGCG CAACUACUCU GACGUCAGAC         50

GACUCGCCCG A                                                  61

(2) INFORMATION FOR SEQ ID NO:90:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE:RNA (ix) FEATURE:

(D) OTHER INFORMATION: All pyrimidines are 2'-F modified (xi) SEQUENCE DESCRIPTION: SEQ ID NO:90:

GGGAGGACGA UGCGGAACAG GUAGUUGGGU GACUCUGUGU GACCUCAGAC          50

GACUCGCCCG A                                                   61

(2) INFORMATION FOR SEQ ID NO:91:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:91:

GGAGGACGAU GCGGAACCAA AUCGUCGAUC UUUCCACCGC UCGUCAGACG          50

ACUCGCCCGA                                                     60

(2) INFORMATION FOR SEQ ID NO:92:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:92:

GGGAGGACGA UGCGGAACCG CUAUUGAAUG UCACUGCUUC GUGCUCAGAC          50

GACUCGCCCG A                                                   61

(2) INFORMATION FOR SEQ ID NO:93:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:93:

GGGAGGACGA UGCGGAACCC AAUCGUCUAA UUCGCUGCUC AUCGUCAGAC          50

GACUCGCCCG A                                                   61

(2) INFORMATION FOR SEQ ID NO:94:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
            (D) OTHER INFORMATION: All pyrimidines are 2'-F modified (xi) SEQUENCE DESCRIPTION: SEQ ID NO:94:

GGGAGGACGA UGCGGAACCC AAUCGUCUAA UUCGCUGCUC AUCGUCAGAC         50

GACUCGCCCG A                                                  61

(2) INFORMATION FOR SEQ ID NO:95:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:95:

GGGAGGACGA UGCGGAACUC AAUGGGCCUA CUUUUCCGUG GUCCUCAGAC         50

GACUCGCCCG A                                                  61

(2) INFORMATION FOR SEQ ID NO:96:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:96:

GGGAGGACGA UGCGGAAGCG GUGAGUCGUG GCUUUCUCCU CGAUCCUCGU         50

CAGACGACUC GCCCGA                                             66

(2) INFORMATION FOR SEQ ID NO:97:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:97:

GGGAGGACGA UGCGGAAGGA UGACGAGGUG GUUGGGGUUU GUGCUCAGAC         50

GACUCGCCCG A                                                  61

(2) INFORMATION FOR SEQ ID NO:98:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
              (D) OTHER INFORMATION: All pyrimidines are 2'-F modified (xi) SEQUENCE DESCRIPTION: SEQ ID NO:98:

GGGAGGACGA UGCGGACAAG ACGAGAACGG GGGGAGCUAC CUGGCCAGAC           50

GACUCGCCCG A                                                    61

(2) INFORMATION FOR SEQ ID NO:99:

(i) SEQUENCE CHARACTERISTICS:
              (A) LENGTH: 61 base pairs
              (B) TYPE: nucleic acid
              (C) STRANDEDNESS: single
              (D) TOPOLOGY: linear (ii) MOLECULE TYPE:RNA (ix) FEATURE:
              (D) OTHER INFORMATION: All pyrimidines are 2'-F modified (xi) SEQUENCE DESCRIPTION: SEQ ID NO:99:

GGGAGGACGA UGCGGAGACA CUAAACAAAU UGGCGACCUG ACCGUCAGAC           50

GACUCGCCCG A                                                    61

(2) INFORMATION FOR SEQ ID NO:100:

(i) SEQUENCE CHARACTERISTICS:
              (A) LENGTH: 69 base pairs
              (B) TYPE: nucleic acid
              (C) STRANDEDNESS: single
              (D) TOPOLOGY: linear (ii) MOLECULE TYPE:RNA (ix) FEATURE:
              (D) OTHER INFORMATION: All pyrimidines are 2'-F modified (xi) SEQUENCE DESCRIPTION: SEQ ID NO:100:

GGGAGGACGA UGCGGAGAGG CUCAGACGAC UCGCCCGACC ACGGAUGCGA           50

CCUCAGACGA CUCGCCCGA                                            69

(2) INFORMATION FOR SEQ ID NO:101:

(i) SEQUENCE CHARACTERISTICS:
              (A) LENGTH: 59 base pairs
              (B) TYPE: nucleic acid
              (C) STRANDEDNESS: single
              (D) TOPOLOGY: linear (ii) MOLECULE TYPE:RNA (ix) FEATURE:
              (D) OTHER INFORMATION: All pyrimidines are 2'-F modified (xi) SEQUENCE DESCRIPTION: SEQ ID NO:101:

GGGAGGACGA UGCGGAGAUG GAUGGAAGUG CUAGUCUUCU GGGGUCAGAC           50

GACUCGCCC                                                       59

(2) INFORMATION FOR SEQ ID NO:102:

(i) SEQUENCE CHARACTERISTICS:
              (A) LENGTH: 62 base pairs
              (B) TYPE: nucleic acid
              (C) STRANDEDNESS: single
              (D) TOPOLOGY: linear

```
    (ii) MOLECULE TYPE:RNA (ix) FEATURE:
         (D) OTHER INFORMATION:  All pyrimidines are 2'-F modified (xi) SEQUENCE DESCRIPTION: SEQ ID NO:102:

GGGAGGACGA UGCGGAGAUG GAUGGAAGUG CUAGUCUUUC UGGGGUCAGA           50

CGACUCGCCC GA                                                   62

(2) INFORMATION FOR SEQ ID NO:103:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
         (D) OTHER INFORMATION:  All pyrimidines are 2'-F modified (xi) SEQUENCE DESCRIPTION: SEQ ID NO:103:

GGGAGGACGA UGCGGAGCAG UUGAAAGACG UGCGUUUCGU UUGGUCAGAC           50

GACUCGCCCG A                                                    61

(2) INFORMATION FOR SEQ ID NO:104:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE:RNA (ix) FEATURE:
         (D) OTHER INFORMATION:  All pyrimidines are 2'-F modified (xi) SEQUENCE DESCRIPTION: SEQ ID NO:104:

GGGAGGACGA UGCGGAGCAC AAUUUUUUCC UUUUCUUUUC GUCCACGUGC           50

UCAGACGACU CGCCCGA                                              67

(2) INFORMATION FOR SEQ ID NO:105:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE:RNA (ix) FEATURE:
         (D) OTHER INFORMATION:  All pyrimidines are 2'-F modified (xi) SEQUENCE DESCRIPTION: SEQ ID NO:105:

GGGAGGACGA UGCGGAGCUG AUGAAGAUGA UCUCUGACCC CUCAGACGAC           50

UCGCCCGA                                                        58

(2) INFORMATION FOR SEQ ID NO:106:

(i) SEQUENCE CHARACTERISTICS:
        (A) LENGTH: 61 base pairs
        (B) TYPE: nucleic acid
        (C) STRANDEDNESS: single
        (D) TOPOLOGY: linear
```

(ii) MOLECULE TYPE:RNA (ix) FEATURE:
            (D) OTHER INFORMATION:   All pyrimidines are 2'-F modified (xi) SEQUENCE DESCRIPTION: SEQ ID NO:106:

GGGAGGACGA UGCGGAGCUG AAAGCGAAGU GCGAGGUGUU UGGUCCAGAC                50

GACUCGCCCG A                                                          61

(2) INFORMATION FOR SEQ ID NO:107:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:   All pyrimidines are 2'-F modified (xi) SEQUENCE DESCRIPTION: SEQ ID NO:107:

GGAGGACGAU GCGGAGCGAA AGUGCGAGUG AUUGACCAGG UGCUCAGACG                 50

ACUCGCCCGA                                                            60

(2) INFORMATION FOR SEQ ID NO:108:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:   All pyrimidines are 2'-F modified (xi) SEQUENCE DESCRIPTION: SEQ ID NO:108:

GGGAGGACGA UGCGGAGCGU GAGAACAGUU GCGAGAUUGC CUGGUCAGAC                 50

GACUCGCCCG A                                                          61

(2) INFORMATION FOR SEQ ID NO:109:

(i) SEQUENCE CHARACTERISTICS:
            (A) LENGTH: 62 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:   All pyrimidines are 2'-F modified (xi) SEQUENCE DESCRIPTION: SEQ ID NO:109:

GGGAGGACGA UGCGGAGGAG AGUGUGGUGA GGGUCGUUUU GAGGGUCAGA                 50

CGACUCGCCC GA                                                         62

(2) INFORMATION FOR SEQ ID NO:110:

(i) SEQUENCE CHARACTERISTICS:
            (A) LENGTH: 61 base pairs
            (B) TYPE: nucleic acid
            (C) STRANDEDNESS: single (D) TOPOLOGY: linear (ii) MOLECULE TYPE:RNA (ix) FEATURE:
        (D) OTHER INFORMATION:   All pyrimidines are 2'-F modified (xi) SEQUENCE DESCRIPTION: SEQ ID NO:110:

GGGAGGACGA UGCGGAGGAG CUGAUGAAGA UGAUCUCUGA CCCCUCAGAC                50

GACUCGCCCG A                                                         61

(2) INFORMATION FOR SEQ ID NO:111:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:   All pyrimidines are 2'-F modified (xi) SEQUENCE DESCRIPTION: SEQ ID NO:111:

GGGAGGACGA UGCGGAGUUC CCAGCCGCCU UGAUUUCUCC GUGGUCAGAC                50

GACUCGCCCG A                                                         61

(2) INFORMATION FOR SEQ ID NO:112:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:   All pyrimidines are 2'-F modified (xi) SEQUENCE DESCRIPTION: SEQ ID NO:112:

GGGAGGACGA UGCGGAUAAG UGCGAGUGUA UGAGGUGCGU GUGGUCAGAC                50

GACUCGCCCG A                                                         61

(2) INFORMATION FOR SEQ ID NO:113:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:   All pyrimidines are 2'-F modified (xi) SEQUENCE DESCRIPTION: SEQ ID NO:113:

GGGAGGACGA UGCGGAUCUG AGGAGCUCUU CGUCGUGCUG AGGGUCAGAC                50

GACUCGCCCG A                                                         61

(2) INFORMATION FOR SEQ ID NO:114:

(i) SEQUENCE CHARACTERISTICS:
        (A) LENGTH: 61 base pairs
        (B) TYPE: nucleic acid (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:114:

GGGAGGACGA UGCGGAUCCG AAUCUUCCUU ACACGUCCUG CUCGUCAGAC           50

GACUCGCCCG A                                                    61

(2) INFORMATION FOR SEQ ID NO:115:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:115:

GGAGGACGAU GCGGAUCCGC AAACCGACAG CUCGAGUUCC GCCUCAGACG            50

ACUCGCCCGA                                                       60

(2) INFORMATION FOR SEQ ID NO:116:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:116:

GGGAGGACGA UGCGGAUGGU ACUUUAGUCU UCCUUGAUUC CGCCUCAGAC           50

GACUCGCCCG A                                                    61

(2) INFORMATION FOR SEQ ID NO:117:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:117:

GGAGGACGAU GCGGAUGAUG ACUGAACGUG CGACUCGACC UGGCCAGACG           50

ACUCGCCCGA                                                      60

(2) INFORMATION FOR SEQ ID NO:118:

(i) SEQUENCE CHARACTERISTICS:
            (A) LENGTH: 60 base pairs (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:118:

GGAGGACGAU GCGGAUGAGG AGGAAGAGUC UGAGGUGCUG GGGUCAGACG         50

ACUCGCCCGA                                                    60

(2) INFORMATION FOR SEQ ID NO:119:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:119:

GGGAGGACGA UGCGGAUUUC GGUCGACUAA AUAGGGGUGG CUCGUCAGAC         50

GACUCGCCCG A                                                  61

(2) INFORMATION FOR SEQ ID NO:120:

(i) SEQUENCE CHARACTERISTICS:
            (A) LENGTH: 68 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:120:

GGGAGGACGA UGCGGCAAGA GGUCAGACGA CUGCCCCGAG UCCUCCCCCG         50

GUCAGACGAC UCGCCCGA                                           68

(2) INFORMATION FOR SEQ ID NO:121:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:121:

GGGAGGACGA UGCGGCAGUG AAAGGCGAGU UUUCUCCUCU CCCUCAGACG         50

ACUCGCCCGA                                                    60

(2) INFORMATION FOR SEQ ID NO:122:

(i) SEQUENCE CHARACTERISTICS:

(A) LENGTH: 61 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:122:

GGGAGGACGA UGCGGCAUCG UUCAGGAGAA UCCACUUCGC CUCGUCAGAC          50

GACUCGCCCG A                                                   61

(2) INFORMATION FOR SEQ ID NO:123:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:123:

GGGAGGACGA UGCGGCAUCU UCCUUGUUCU UCCAACCGUG CUCCUCAGAC          50

GACUCGCCCG A                                                   61

(2) INFORMATION FOR SEQ ID NO:124:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:124:

GGGAGGACGA UGCGGCAUCG UAAACAAUUU GUUCCAUCUC CGCCUCAGAC          50

GACUCGCCCG A                                                   61

(2) INFORMATION FOR SEQ ID NO:125:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:125:

GGGAGGACGA UGCGGCAUUG UCCAAGUUUA GCUGUCCGUG CUCGUCAGAC          50

GACUCGCCCG A                                                   61

(2) INFORMATION FOR SEQ ID NO:126:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:126:

GGGAGGACGA UGCGGCAUAG UCCGGAUACU AGUCACCAGC CUCGUAGACG          50

ACUCGCCCGA                                                     60

(2) INFORMATION FOR SEQ ID NO:127:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:127:

GGGAGGACGA UGCGGCCGUC UCGAUCCUUC UAUGCCUUCG CUCGUCAGAC          50

GACUCGCCCG A                                                   61

(2) INFORMATION FOR SEQ ID NO:128:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:128:

GGGAGGACGA UGCGGCGGGA AGUUUGAGGU GUANUACCUG UUGUCUGGUC          50

AGACGACUCG CCCGA                                               65

(2) INFORMATION FOR SEQ ID NO:129:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:129:

GGGAGGACGA UGCGGCUCAA CUCUCCCACA GACGACUCGC CCGGGCCUCC          50

UCAGACGACU CGCCCGA                                             67

(2) INFORMATION FOR SEQ ID NO:130:

(i) SEQUENCE CHARACTERISTICS:
            (A) LENGTH: 58 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:130:

GGGAGGACGA UGCGGGACUC CUCGACCGAC UCGACCGGCU CGUCAGACGA           50

CUCGCCGA                                                         58

(2) INFORMATION FOR SEQ ID NO:131:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:131:

GGAGGACGAU GCGGGAACCA AAUCGUCGAU CUUUCCACCG CUCGUCAGAC           50

GACUCGCCCG A                                                    61

(2) INFORMATION FOR SEQ ID NO:132:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:132:

GGGAGGACGA UGCGGGACCA CCUCGAUCCU CAGCGCCAUU GCCCUCAGAC           50

GACUCGCCCG A                                                    61

(2) INFORMATION FOR SEQ ID NO:133:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE:RNA (ix) FEATURE:
            (D) OTHER INFORMATION:  All pyrimidines are 2'-F modified (xi) SEQUENCE DESCRIPTION: SEQ ID NO:133:

GGGAGGACGA UGCGGGAAGU GGAAGGGUAG UUGUGUGACC UCAGACGACU           50

CGCCCGA                                                         57

(2) INFORMATION FOR SEQ ID NO:134:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:134:

```
CGGAGGACGA UGCGGGCAAA CUUUUCCUUU UCCCUUUAUC UUCCUUGCCC         50

UCAGACGACU CGCCCGA                                             67
```

(2) INFORMATION FOR SEQ ID NO:135:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:135:

```
GGGAGGACGA UGCGGGGCCG ACGAUUCACC AAUGUUCUCU CUGGUCAGAC         50

GACUCGCCCG A                                                   61
```

(2) INFORMATION FOR SEQ ID NO:136:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:136:

```
GGAGGACGAU GCGGGGUUCC UCAAUGACGA UCUCCAUUCC GCUCGUCAGA         50

CGACUCGCCC AG                                                  62
```

(2) INFORMATION FOR SEQ ID NO:137:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:137:

```
GGAGGACGAU GCGGGUCGAC AUUGAAGCUG CUCUGCCUUG AUCCUCAGAC         50

GACUCGCCCG A                                                   61
```

(2) INFORMATION FOR SEQ ID NO:138:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:138:

```
GGGAGGACGA UGCGGUCCAA UUCGUUCUCA UGCCUUUCCG CUCGUCAGAC         50

GACUCGCCCG A                                                   61
```

(2) INFORMATION FOR SEQ ID NO:139:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:139:

```
GGGAGGACGA UGCGGUCCGC AAGUUUAGCA CUCACUGCCU CGUCAGACGA         50

CUCGCCCGA                                                      59
```

(2) INFORMATION FOR SEQ ID NO:140:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:140:

```
GGGAGGACGA UGCGGUCCAC AUCGAAUUUU CUGUCCGUUC GUCAGACGAC         50

UCGCCCGA                                                       58
```

(2) INFORMATION FOR SEQ ID NO:141:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:141:

```
GGGAGGACGA UGCGGUCGAU GUUCUUCCUC ACCACUGCUC GUCGCCUCAG         50

ACGACUCGCC CGA                                                 63
```

(2) INFORMATION FOR SEQ ID NO:142:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:142:

```
GGGAGGACGA UGCGGUCGAG CUGAGAGGGG CUACUUGUUC UGGUCACAGA          50

CGACUCGCCC GA                                                   62
```

(2) INFORMATION FOR SEQ ID NO:143:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:143:

```
GGGAGGACGA UGCGGUGGAA GCGAAUGGGC UAGGGUGGGC UGACCUCCAG          50

ACGACUCGCC CGA                                                  63
```

(2) INFORMATION FOR SEQ ID NO:144:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:144:

```
GGGAGGACGA UGCGGUGGAC UUCUUUUCCU CUUCCUCCUU CCGCCGGUCA          50

GACGACUCGC CCGA                                                 64
```

(2) INFORMATION FOR SEQ ID NO:145:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:145:

```
GGAGGACGAU GCGGUUCCAA AUCGUCUAAG CAUCGCUCGC UCGUCAGACG          50
```

ACUCGCCCAG 60

(2) INFORMATION FOR SEQ ID NO:146:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:146:

GGGAGGACGA UGCGGUUCCA CAUCGCAAUU UUCUGUCCGU GCUCGUCAGA 50

CGACUCGCCC GA 62

(2) INFORMATION FOR SEQ ID NO:147:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:147:

GGGAGGACGA UGCGGUUCCA CAUCGAAUUU UCUGUCCGUG UCGUCAGACG 50

ACUCGCCCGA 60

(2) INFORMATION FOR SEQ ID NO:148:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:148:

GGGAGGACGA UGCGGUUCCG AUCGACUCCA CAUACAUCUG CUCGUCAGAC 50

GACUCGCCCG A 61

(2) INFORMATION FOR SEQ ID NO:149:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:149:

GGGAGGACGA UGCGGUUCCG ACAUCGAUGU UGCUCUUCGC CUCGUCAGAC 50

```
GACUCGCCCG A                                                          61

(2) INFORMATION FOR SEQ ID NO:150:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:150:

GGGAGGACGA UGCGGUUCCG AAGUUCUUCC CCCGAGCCUU CCCCCUCCAG                 50

ACGACUCGCC CGA                                                        63

(2) INFORMATION FOR SEQ ID NO:151:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:151:

GGGAGGACGA UGCGGUUCCG ACGAUUCUCC AAUGUUCUCU CUGGUCAGAC                 50

GACUCGCCCG A                                                          61

(2) INFORMATION FOR SEQ ID NO:152:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:152:

GGGAGGACGA UGCGGUUCCG ACGAUUCUCC AAUCUUCUCU CUGGUCAGAC                 50

GACUCGCCCG A                                                          61

(2) INFORMATION FOR SEQ ID NO:153:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION:  All pyrimidines are 2'-F modified (xi) SEQUENCE DESCRIPTION: SEQ ID NO:153:
```

```
GGGAGGACGA UGCGGUUCCG CAAGUUUAGA CACUCACUGC CUCGUCAGAC        50

GACUCGCCCG A                                                  61
```

(2) INFORMATION FOR SEQ ID NO:154:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:154:

```
GGGAGGACGA UGCGGUUCCG CAAAGUAGAU AUNUCAUCCG CACGUCAGAC        50

GACUCGCCCG A                                                  61
```

(2) INFORMATION FOR SEQ ID NO:155:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:RNA (ix) FEATURE:
        (D) OTHER INFORMATION: All pyrimidines are 2'-F modified (xi) SEQUENCE DESCRIPTION: SEQ ID NO:155:

```
GGGAGGACGA UGCGGUUGAG UGGACAGUGC GAUUCGUUUU GGGGUCAGAC        50

GACUCGCCCG A                                                  61
```

(2) INFORMATION FOR SEQ ID NO: 156:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE:DNA (ix) FEATURE:
        (D) OTHER INFORMATION: All nucleotides are bound by a
            phosphorothioate linkage (xi) SEQUENCE DESCRIPTION: SEQ ID NO: 156:

```
GGCGGGGCTA CGTACCGGGG CTTTGTAAAA CCCCGCC                      37
```

(2) INFORMATION FOR SEQ ID NO: 157:

(i) SEQUENCE CHARACTERISTICS:
        (A) LENGTH: 25 base pairs
        (B) TYPE: nucleic acid
        (C) STRANDEDNESS: single
        (D) TOPOLOGY: linear -continued

```
(ii) MOLECULE TYPE:DNA (ix) FEATURE:
     (D) OTHER INFORMATION:  All nucleotides are bound by a
         phosphorothioate linkage (xi) SEQUENCE DESCRIPTION: SEQ ID NO: 157:

CTCTCGCACC CATCTCTCTC CTTCT                                               25
```